United States Patent [19]

Levitt

[11] Patent Number: 4,544,401

[45] Date of Patent: Oct. 1, 1985

[54] AGRICULTURAL PYRIDINESULFONAMIDES

[75] Inventor: George Levitt, Wilmington, Del.

[73] Assignee: E. I. Du Pont de Nemours and Company, Wilmington, Del.

[21] Appl. No.: 227,243

[22] Filed: Jan. 22, 1981

Related U.S. Application Data

[63] Continuation-in-part of Ser. No. 83,753, Oct. 23, 1979, abandoned, which is a continuation-in-part of Ser. No. 966,258, Dec. 4, 1978, abandoned.

[51] Int. Cl.⁴ .................. A01N 43/54; C07D 239/28; C07D 239/30
[52] U.S. Cl. ........................................ 71/92; 71/93; 544/182; 544/204; 544/212; 544/310; 544/317; 544/320; 544/324; 544/326; 544/327; 544/328; 544/331
[58] Field of Search .............. 544/212, 320, 331, 324; 71/92

[56] References Cited

U.S. PATENT DOCUMENTS 4,244,950  1/1981  Bidder et al. ................... 424/248.5

FOREIGN PATENT DOCUMENTS 1468747  2/1967  France .
121788  9/1966  Netherlands .

OTHER PUBLICATIONS

Logemann et al., Chem. Abst., vol. 53, (1959), 18052g.
Boggiano et al., J. Pharmacy and Pharmacology, vol. 13, (1961), 567–574.
Levitt, German Offen. 2,715,786, Chem. Abst., vol. 88, (1978), 6935x.
Wojciechowski, J. Acta. Polon. Pharm., vol. 19, (1962), pp. 121–125.
Delarge, Acta Pol. Pharm., vol. 34, (1977), pp. 245–249.

Primary Examiner—Catherine L. Mills

[57] ABSTRACT

N-(heterocyclicaminocarbonyl)pyridinesulfonamides; are useful for the regulation of plant growth and as pre-emergence and post-emergence herbicides.

26 Claims, No Drawings

AGRICULTURAL PYRIDINESULFONAMIDES

RELATED APPLICATIONS

This application is a continuation-in-part of my copending application U.S. Ser. No. 083,753 filed Oct. 23, 1979, now abandoned which is a continuation-in-part of my copending application U.S. Ser. No. 966,258, filed Dec. 4, 1978, now abandoned.

BACKGROUND OF THE INVENTION

This invention relates to pyridinesulfonamides which are useful as agricultural chemicals.

French Pat. No. 1,468,747 discloses the following para-substituted phenylsulfonamides, useful as anti-diabetic agents:

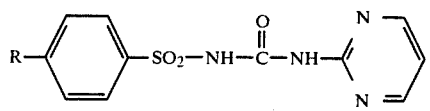

wherein R=H, halogen, $CF_3$ or alkyl.

Logemann et al. Chem. Ab., 53, 18052 g (1959), disclose a number of sulfonamides, including uracil derivatives and those having the formula:

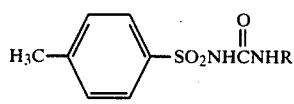

wherein R is butyl, phenyl or

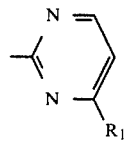

and $R_1$ is hydrogen or methyl. When tested for hypoglycemic effect in rats (oral doses of 25 mg/100 g), the compounds in which R is butyl and phenyl were most potent.

Wojciechowski, J. Acta. Polon. Pharm. 19, p. 125–5 (1962) [Chem. Ab., 59 1633 e] describes the synthesis of N-[(2,6-dimethoxypyrimidin-4-yl)aminocarbonyl]-4-methylbenzenesulfonamide:

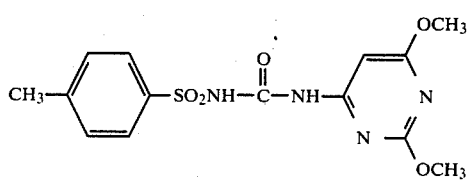

Based upon similarity to a known compound, the author predicted hypoglycemic activity for the foregoing compound.

Netherlands Pat. No. 121,788, published Sept. 15, 1966, teaches the preparation of compounds of Formula (i), and their use as general or selective herbicides,

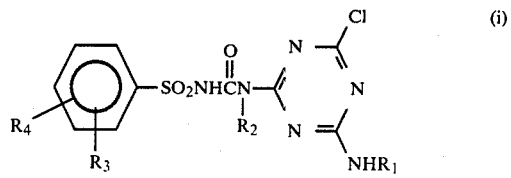

wherein $R_1$ and $R_2$ may independently be alkyl of 1–4 carbon atoms; and $R_3$ and $R_4$ may independently be hydrogen, chlorine or alkyl of 1–4 carbon atoms.

Compounds of Formula (ii), and their use as antidiabetic agents, are reported in J. Drug. Res. 6, 123 (1974).

wherein R is pyridyl.

In U.S. Ser. No. 029,821, herbicidal compounds such as N-heterocyclic-N'(arylsulfonyl)carbamimidothioates (or compounds wherein a thienyl radical is substituted for the aryl radical), such as methyl N'-(2-chlorophenylsulfonyl)-N-(4-methoxy-6-methylpyrimidin-2-yl)carbamimidothioate are taught.

United States Pat. No. 3,689,549 F (Sept. 5, 1972) to R. P. Williams discloses "heterocyclic sulfonamides wherein the heteroatoms are inert can be used, e.g., compounds having the furan, thiophene or pyridine nucleus," in the production of sulfonyl isocyanates from sulfonamides in a sulfolane solvent.

B. G. Boggiano, V. Petrow, O. Stephenson and A. M. Wild, in Journal of Pharmacy and Pharmacology 13, 567–574 (1961) disclose the following compounds which were tested for hypoglycemic activity.

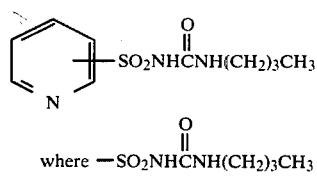

where $-SO_2NHCNH(CH_2)_3CH_3$ is in 2 or 3 position.

J. Delarge in Acta Pol. Pharm. 34, 245–249 (1977) discloses N-alkylcarbamoylpyridinesulfonamides, as described in the structure below, as mild antiinflammatory agents and strong diuretics.

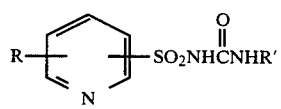

R=3-, 4-, 5-, 6-Me, 2-, 4-, 6-Cl, 3-Br, 4-$ET_2N$, 4-$Me_2CHNH$, 4-(3-$ClC_6H_4$)NH, 4-(3-$CF_3C_6H_4$)NH
R'=Et, Pr, $Me_2CH$, Bu

in 2, 3 and 4 position.

German Pat. No. 2,516,025 (Nov. 6, 1975) to J. E. Delarge, C. L. Lapiere and A. H. Georges discloses the following compounds as inflammation inhibitors and diuretics.

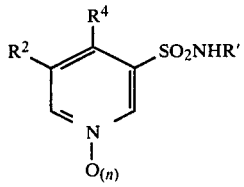

$R^4 = XR$

R=$C_6H_4R^3$($R^3$=Cl, $CF_3$, Me, MeO, H, Br, F, $NO_2$, Et, $NH_2$), Et, iso-Pr, 4-methylfuryl, $C_6H_3Cl_2$-, $C_6H_3(CF_3)Cl$;

R'=alkylcarbamoyl, cyclohexylcarbamoyl, arylcarbamoyl, $CSNHCH_2CH=CH_2$, $CONHC_6H_4Cl$-p, alkylthiocarbamoyl, H, COEt;

$R^2$=H, Me;

X=NH, NMe, O, S, NEt; and n=0,1.

United States Pat. No. 3,346,590 (Oct. 10, 1967) (to K. Dickere and E. Kühle) discloses the following pyridinesulfonyl isothiocyanates as novel compounds.

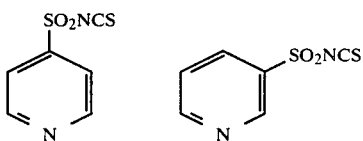

The presence of undesired vegetation causes substantial damage to useful crops, especially agricultural products that satisfy man's basic food and fiber needs, such as cotton, rice, corn, wheat, soybean and the like. The current population explosion and concomitant world food and fiber shortage demand improvements in the efficiency of producing these crops. Preventing or minimizing the loss of a portion of such valuable crops by killing or inhibiting the growth of undesired vegetation is one way of improving this efficiency.

A wide variety of materials useful for killing or inhibiting (controlling) the growth of undesired vegetation is available; such materials are commonly referred to as herbicides. The need exists, however, for still more effective herbicides that destroy or control weeds without causing significant damage to useful crops.

SUMMARY OF THE INVENTION

The invention relates to compounds of Formula I and their agriculturally suitable salts, suitable agricultural compositions containing them and methods of using them as general and selective pre-emergence and post-emergence herbicides and as plant growth regulators.

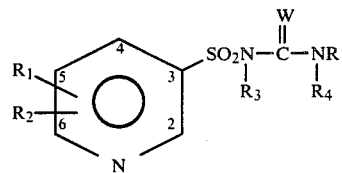

wherein

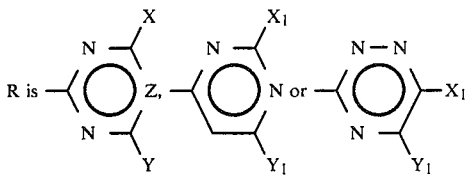

$R_1$ is H, Cl, Br, F, $C_1$-$C_4$ alkyl, $C_1$-$C_4$ alkoxy, $C_1$-$C_4$ alkylthio, $COR_5$, $NR_6R_7$ or $SO_2NR_{10}R_{11}$;

$R_2$ is H, Cl, Br or $CH_3$;

$R_3$ and $R_4$ are independently H or $CH_3$;

$R_5$ is $C_1$-$C_6$ alkyl, $C_3$-$C_6$ alkenyl, $CH_2CH_2OCH_3$, $CH_2CH_2OCH_2CH_3$, $CH_2CH_2CH_2OCH_3$ or $CH_2CH_2Cl$;

$R_6$ and $R_7$ are independently $CH_3$ or $CH_3CH_2$, or $R_6$ and $R_7$ can be taken together to form —$(CH_2)_4$—, —$(CH_2)_5$— or —$CH_2CH_2OCH_2CH_2$—;

$R_{10}$ and $R_{11}$ are independently $CH_3$ or $CH_3CH_2$;

W is oxygen or sulfur;

X is $CH_3$, —$OCH_3$ or —$OCH_2CH_3$;

Y is H, Cl, $CH_3$, $CF_3$, —$NHCH_3$, —$N(CH_3)_2$, —$CH_2OR_8$, —$CH_2CH_2OR_8$, —$OCH_2CF_3$ or $VR_9$;

Z is CH or N;

V is oxygen or sulfur;

$R_8$ is $CH_3$ or $CH_3CH_2$;

$R_9$ is $CH_3$, $CH_3CH_2$, $CH_2CH_2OR_8$, $CH_2CO_2R_8$,

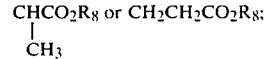

$Y_1$ is H, $CH_3$ or $OCH_3$; and $X_1$ is H, Cl, —$OCH_3$, —$OCH_2CH_3$, or $CH_3$;

and agricultural salts thereof; providing that:

(1) both $X_1$ and $Y_1$ are not simultaneously hydrogen;

(2) when R is

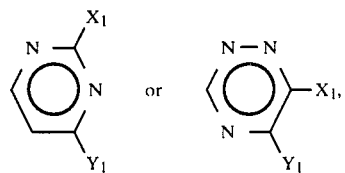

then $R_3$ and $R_4$ are both H; and (3) $R_1$ is at the 2- or 4-position of the pyridine ring.

Preferred Compounds

Preferred in order of increasing activity and/or increasingly favorable ease of synthesis are:

(1) Compounds of the generic scope wherein $R_3$ is H and W is oxygen;

(2) Compounds of Preferred (1) wherein $R_2$ is hydrogen;

(3) Compounds of Preferred (2) wherein $R_1$ is Cl, $CH_3O$ or $CH_3$;

(4) Compounds of Preferred (3) which are 2- or 4-chloro-3-pyridyl sulfonyl compounds;

(5) Compounds of the generic scope or Preferred (1) (4) wherein

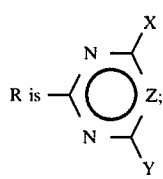

(6) Compounds of Preferred (5) wherein $R_4$ is hydrogen;

(7) Compounds or Preferred (5) wherein $R_1$ is chlorine;

(8) Compounds of Preferred (5) wherein X is $CH_3$ or $-OCH_3$; and Y is $CH_3$, $-OCH_3$, $OCH_2CH_3$ or $-CH_2OCH_3$.

More Preferred still for their higher activity and/or more favorable ease of synthesis are those compounds of Preferred (8) wherein $R_3$ and $R_4$ are hydrogen and W is oxygen.

Specifically Preferred compounds are:

(1) 2-Chloro-N-[(4-methoxy-6-methylpyrimidin-2-yl)aminocarbonyl)]-3-pyridinesulfonamide;

(2) 2-Chloro-N-[(4,6-dimethoxypyrimidin-2-yl)aminocarbonyl]-3-pyridinesulfonamide;

(3) 2-Chloro-N-[(4,6-dimethylpyrimidin-2-yl)aminocarbonyl]-3-pyridinesulfonamide;

(4) 2-Chloro-N-[(4-methoxy-6-methyl-1,3,5-triazin-2-yl)aminocarbonyl]-3-pyridinesulfonamide;

(5) 2-Chloro-N-[(4,6-dimethyl-1,3,5-triazin-2-yl)aminocarbonyl]-3-pyridinesulfonamide; and (6) 2-Chloro-N-[(4,6-dimethoxy-1,3,5-triazin-2-yl)aminocarbonyl]-3-pyridinesulfonamide.

Synthesis

The synthesis of pyridinesulfonylisocyanates, the compounds of Formula IIIA can be carried out by reacting a suitably substituted N-(alkylaminocarbonyl)-pyridinesulfonamide with phosgene in a refluxing solvent such as xylene or chlorobenzene followed by filtration of the solution at room temperature and removal of the solvent. This reaction is shown in Equation 1.

Equation 1

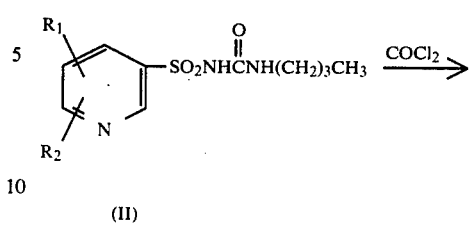

wherein $R_1$ and $R_2$ are as previously defined.

N-(alkylaminocarbonyl)pyridinesulfonamides of Formula II may be conveniently prepared by the reaction of equimolar amounts of an appropriate pyridinesulfonamide, an alkyl isocyanate and an anhydrous base such as $K_2CO_3$ or $CaCO_3$ in an anhydrous solvent such as acetone or acetonitrile. Addition of water and adjustment of the pH to about 3 with HCl, followed by filtration yields the desired N-(alkylaminocarbonyl)-pyridinesulfonamides.

Pyridinesulfonylisothiocyanates of Formula IIIB can be prepared according to the procedure taught by K. Dickere and E. Kuhle in United States Pat. No. 3,346,590 (10/10/1967) whereby a suitable pyridinesulfonyliminodithiocarbonate IV is reacted with phosgene in the presence of a solvent such as toluene or xylene. The procedure is illustrated in Equation 2.

Equation 2

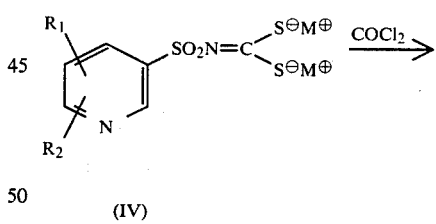

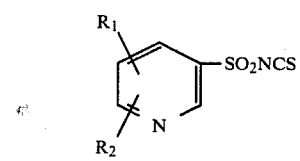

wherein $R_1$ and $R_2$ are as previously defined.

Compounds of Formula I are conveniently prepared by reacting an appropriately substituted pyridinesulfonylisocyanate or pyridinesulfonylisothiocyanate of Formula III with an appropriately substituted amino pyrimidine or amino triazine of Formula V, according to the procedure of Equation 3.

Equation 3

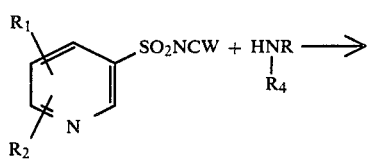

(III)   (V)

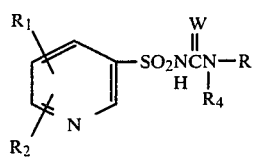

(I)

wherein R, $R_1$, $R_2$, $R_4$ and W are as previously defined.

The reaction of Equation 3 is best carried out in inert aprotic organic solvents such as methylene chloride, tetrahydrofuran or acetonitrile, at ambient pressure and temperature. The mode of addition is not critical; however, it is often convenient to add the sulfonyl isocyanate or isothiocyanate to a stirred suspension of amine V. Since such isocyanates and isothiocyanates are liquids, low melting solids or are readily soluble in solvents such as those listed above, their addition can be easily controlled.

The reaction is generally exothermic. In some cases, the desired product is soluble in the warm reaction medium and on cooling crystallizes in pure form. Other products which are soluble in the reaction mixture are isolated by evaporation of the solvent, trituration of the solid residue with solvents such as 1-chlorobutane or ethyl ether, and filtration.

As shown in Equation 4, compounds of Formula Ia, wherein $R_3$ is methyl and W is O, can be prepared by methylation of salts VI wherein M is an alkali metal cation such as sodium (derived from compounds of Formula Ia, wherein $R_3$ is hydrogen).

Equation 4

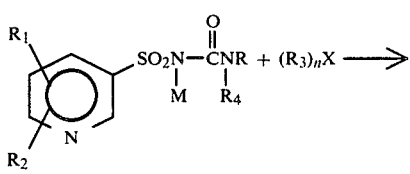

(VI)   (VII)

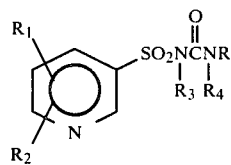

(Ia)

X being an incipient anion and n being an integer corresponding to the valence of X.

The reaction of Equation 4 is best carried out in aprotic organic solvents such as tetrahydrofuran, dimethylformamide, or dimethylacetamide, at ambient temperature. Methylating agents VII, such as dimethyl sulfate or methyl iodide, can be employed. The desired product can be isolated by pouring the reaction mixture into water and filtering off the precipitated solid.

As shown in Equation 5, compounds of Formula Ia' wherein R and $R_4$ are as defined previously, can also be prepared by the reaction of an appropriately substituted pyridyl sulfonyl-N-methylcarbamyl chloride or sulfonyl-N-methylthiocarbamyl chloride of Formula VIII with an appropriate aminopyrimidine or aminotriazine of Formula V.

Equation 5

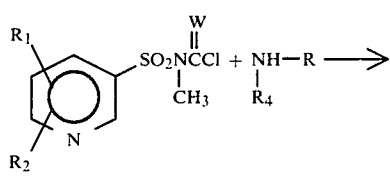

(VIII)   (V)

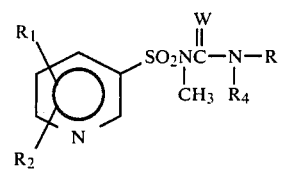

(Ia')

wherein R, $R_1$, $R_2$, $R_4$ and W are as previously defined.

The preparation of ureas and thioureas, like those of Formula I, from amines and carbamyl chlorides and thiocarbamyl chlorides is well known to the art. The reaction can best be carried out by adding equivalent amounts of the chloride VIII and amine V to an inert organic solvent, such as tetrahydrofuran, xylene, or methylene chloride, in the presence of acid acceptor, such as triethylamine, pyridine, or sodium carbonate employing temperatures from 20° to 130°. Soluble products can be isolated by filtering off precipitated salts and concentration of the filtrate. Insoluble products can be filtered off and washed free of salts with water.

The chlorides of Formula VIII can be prepared by phosgenation or thiophosgenation of N-alkylsulfonamide metal salts. The sulfonamide salt is added to an excess of phosgene or thiophosgene in an inert organic solvent, such as tetrahydrofuran, toluene, or xylene, whereupon, after removal of the excess phosgene, the chloride VIII can be isolated or reacted in situ with the amine V.

Compounds of Formula I, wherein R and $R_4$ are defined previously can also be prepared by the reaction scheme shown in Equations 6, 7 and 8.

Equation 6

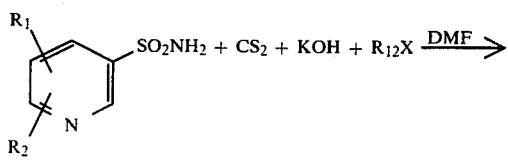

(IXA)

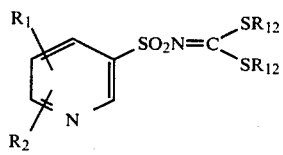

(X)

wherein $R_1$ and $R_2$ are as previously defined.

Dialkyl esters of N-(pyridinylsulfonyl)carbonimidothioic acids of Formula X wherein $R_{12}$ is $C_1$-$C_5$ alkyl, can be conveniently prepared by the reaction of an appropriate pyridinesulfonamide, carbon disulfide, an alkali metal hydroxide and an alkyl halide in a suitable solvent, such as dimethylformamide or dimethylsulfoxide at ambient temperature. Good yields can be obtained if alkali metal hydroxide and carbon disulfide are added in portions to the solution of pyridinesulfonamide, followed by a dropwise addition of the alkyl halide. The reaction is generally exothermic. The desired product can be isolated by pouring the reaction mixture into cold water and filtering off the precipitated solid.

Equation 7

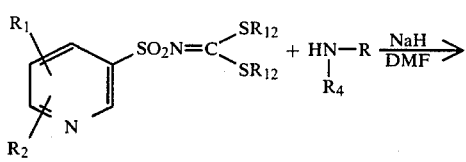

(X)    (V)

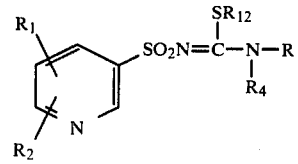

(XI)

wherein R, $R_1$, $R_2$, $R_4$ and $R_{12}$ are as previously defined.

The reaction of Equation 7 is best carried out in inert aprotic solvents, such as tetrahydrofuran, N,N-dimethylformamide, or dimethylacetamide at ambient temperature. The anion of the aminopyrimidine or aminotriazine can be prepared by the reaction of an alkali metal hydride with an appropriate amine V and a compound of Formula X is added to the stirred solution of the anion species at ambient temperature. Addition of water, followed by filtration, yields the desired solid product.

Pyridinylsulfonylcarbonimidothioic acid esters of Formula XI, as prepared in Equation 7 can be converted to the corresponding N-(pyrimidinyl or triazinyl aminocarbonyl)pyridinesulfonamides according to Equation 8.

Equation 8

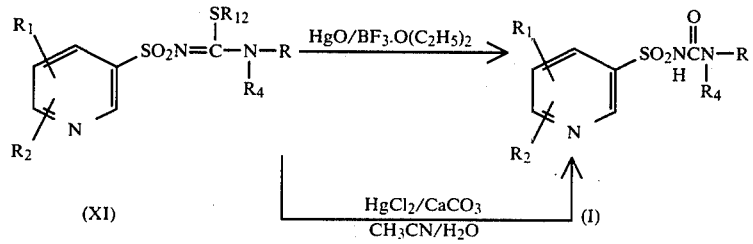

wherein R, $R_1$, $R_2$, $R_4$ and $R_{12}$ are as previously defined.

The reaction of Equation 8 is best carried out in aqueous tetrahydrofuran, or aqueous acetonitrile. Oxidizing agents, such as mercuric oxide/boron trifluoride etherate, or mercuric chloride/calcium carbonate may be employed at temperatures of 20° to 130° C. The desired product can be filtered off and washed free of salts with water.

As shown in Equation 9, compounds of Formula Ib, wherein R, $R_1$, $R_2$ and $R_3$ are as previously defined are alternatively prepared by the reaction of an appropriately substituted pyridylsulfonamide with the appropriate triazine or pyrimidine isothiocyanate of Formula XII.

Equation 9

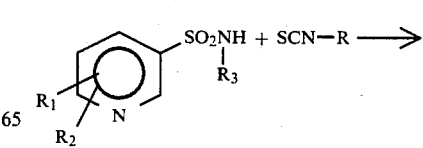

(IX)    (XII)

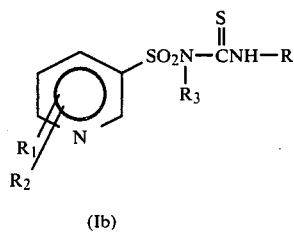

(Ib)

The reaction of Equation 9 is best carried out by dissolving or suspending the sulfonamide and isothiocyanate in a polar solvent such as acetone, acetonitrile, ethyl acetate or methylethylketone, adding an equivalent of a base such as potassium carbonate and stirring the mixture at ambient temperature up to the reflux temperature for one to twenty-four hours. In some cases, the product precipitates from the reaction mixture and can be removed by filtration. The product is stirred in dilute mineral acid, filtered and washed with cold water. If the product does not precipitate from the reaction mixture it can be isolated by evaporation of the solvent, trituration of the residue with dilute mineral acid and filtering off the insoluble product.

The heterocyclic isothiocyanates which are used in the procedure of Equation 9 are prepared, for example, according to the method of Japan patent application Pub: Kokai 51-143686, June 5, 1976, or that of W. Abraham and G. Barnikow, Tetrahedron 29, 691-7 (1973).

N-(Triazinyl or pyrimidinylaminothioxomethyl)-pyridinesulfonamides wherein R, $R_1$, $R_2$, $R_3$, and $R_4$ are as defined previously can be converted to the corresponding aminocarbonylpyridinesulfonamides as shown in Equation 9A.

Equation 9A

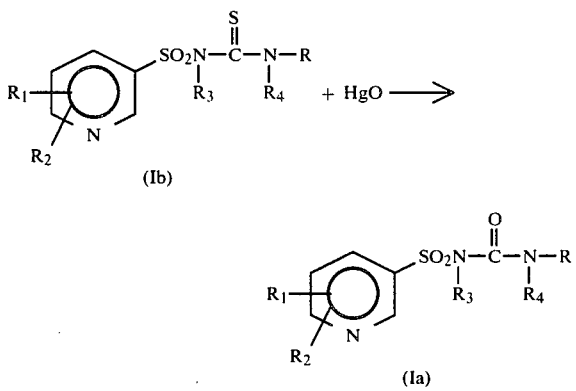

The reaction of Equation 9A is best carried out by suspending the appropriate compound of Formula Ib and mercuric oxide in a solvent such as acetone, acetonitrile or methylethyl ketone and stirring the mixture at ambient temperature for 10 to 72 hours. Filtration to remove the insoluble mercury compound and evaporation of the solvent yields a residue containing the desired product.

Compounds of formula I, where $R_1 \neq CO_2R_5$, are conveniently prepared by reacting the appropriately substituted pyridinesulfonamide with the appropriate methyl pyrimidinyl carbamate or methyl triazinyl carbamate of Formula XIII in the presence of an equimolar amount of trimethylaluminum according to the procedure of Equation 10.

Equation 10

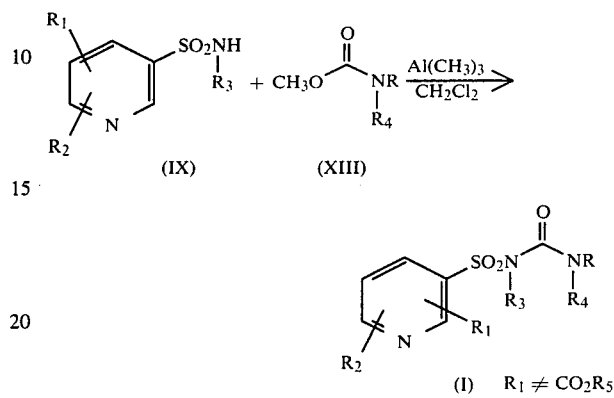

The reaction of Equation 10 is best carried out in methylene chloride at 25° to 40° for 24 to 96 hours under a nitrogen atmosphere. The product is isolated by the addition of an aqueous acetic acid solution followed by extraction of the product into methylene chloride or direct filtration of a product of low solubility. The product is purified by trituration with solvents such as ether or subjected to column chromatography.

The procedure for the preparation of agriculturally suitable salts of the compounds of Formula I is described for alkali metal salts, ammonium salts and acid addition salts in Equations 11, 12 and 13 respectively. Preparation of other salts would be obvious to one skilled in the art.

Equation 11

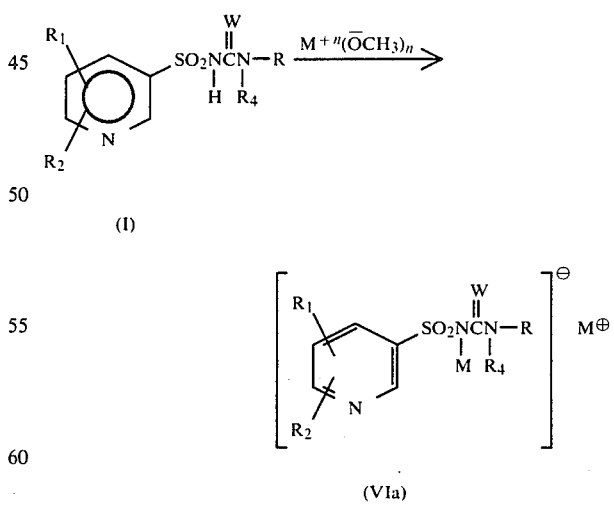

wherein R, $R_1$, $R_2$, $R_4$ and W are as previously defined.

The reaction of Equation 11 is best carried out by adding to a suspension of one equivalent of the appropriate pyridinesulfonamide in a solvent such as methanol or ethanol one equivalent of an appropriate base such as a metal alkoxide, hydroxide, or carbonate in the same solvent. Following heating at 40°–50° the solvent is removed in vacuo to yield the desired salt which can be triturated with solvents such as ethylacetate, ethylether or hexane to give the desired solid alkali metal salts.

Equation 12

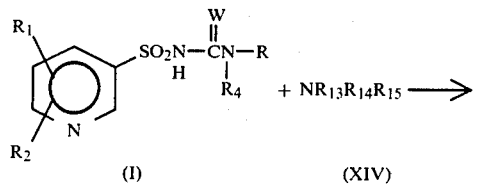

(I)    (XIV)

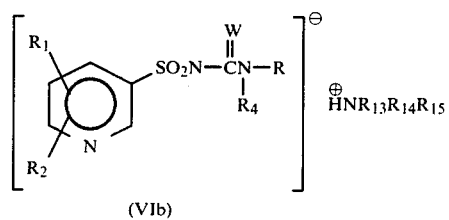

(VIb)

wherein $R_{13}$ is $C_1-C_{12}$ alkyl, $CH_2CH_2OH$, $C_6H_5$ or H
$R_{14}$ is $C_1-C_{12}$ alkyl, $CH_2CH_2OH$, $C_6H_5$ or H
$R_{15}$ is $C_1-C_{12}$ alkyl, $CH_2CH_2OH$, $C_6H_5$ or H

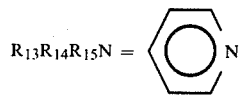

with the proviso that $R_{13}$, $R_{14}$ and $R_{15}$ cannot all be phenyl at the same time.

The ammonium salts of substituted pyridinesulfonamides can be prepared as described in Equation 12.

Generally, one equivalent of an appropriate amine such as ammonia, dimethylamine, diethanolamine or ethanolamine is added neat or in a solvent such as methylene chloride or methanol to a suspension of the appropriate benzenesulfonamide in the same solvent. The solvent is removed under reduced pressure to yield as product the desired salt.

Equation 13

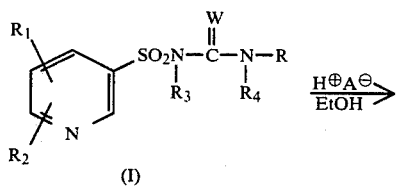

(I)

-continued

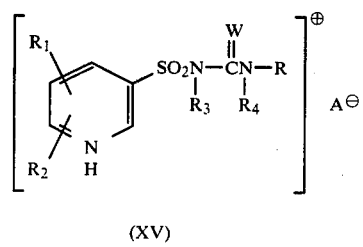

(XV)

As shown in Equation 13, the acid addition salts of N-(heterocyclicaminocarbonyl)pyridinesulfonamides of Formula X can be prepared by heating at about 40°–50° a suspension of the aminocarbonylpyridinesulfonamide in a solvent such as ethanol or hexane containing an equivalent amount of an acid such as HCl, HBr, $H_2SO_4$, p-toluenesulfonic acid or trichloroacetic acid. In the case of volatile mineral acids such as HCl or organic acids such as trichloro acetic acid an excess may be employed. Removal of solvent in vacuo yields the desired salt.

The synthesis of sulfur compounds of pyridine has been reviewed in "The Chemistry of Heterocyclic Compounds", a series published by Interscience Publ., New York and London. Pyridinesulfonamides are described by H. L. Tale in "Pyridine and Its Derivatives" Supplement, Part 4 (1975) which is herein incorporated by reference.

Those intermediate sulfonamides of Formula IX not described in the aforementioned reference may be prepared by conventional methods, including nucleophilic displacement of the known 2- and 4-halopyridine-3-sulfonamides of Formula XVI. These are illustrated in Equations 14 and 15.

Equation 14

$R_1=NR_6R_7$, $C_1-C_4$ alkoxy, $C_1-C_4$ alkylthio, F,

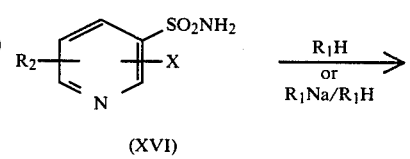

(XVI)

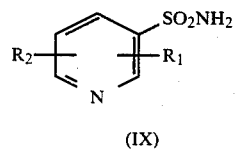

(IX)

X = Cl, Br
$R_2$ = H, $CH_3$, Cl, Br

Equation 15

$R_1=CO_2R_5$,

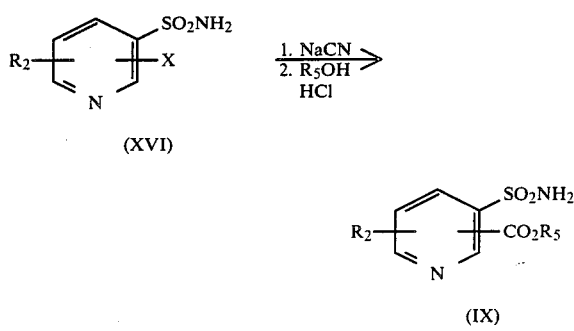

(XVI)

X = Cl, Br
R$_2$ = H, CH$_3$, Cl, Br

The intermediate pyridinesulfonamides of Formula IX where R$_1$ is SO$_2$NR$_{10}$R$_{11}$ may be prepared by the sequence of reactions as shown in Equation 16.

Equation 16

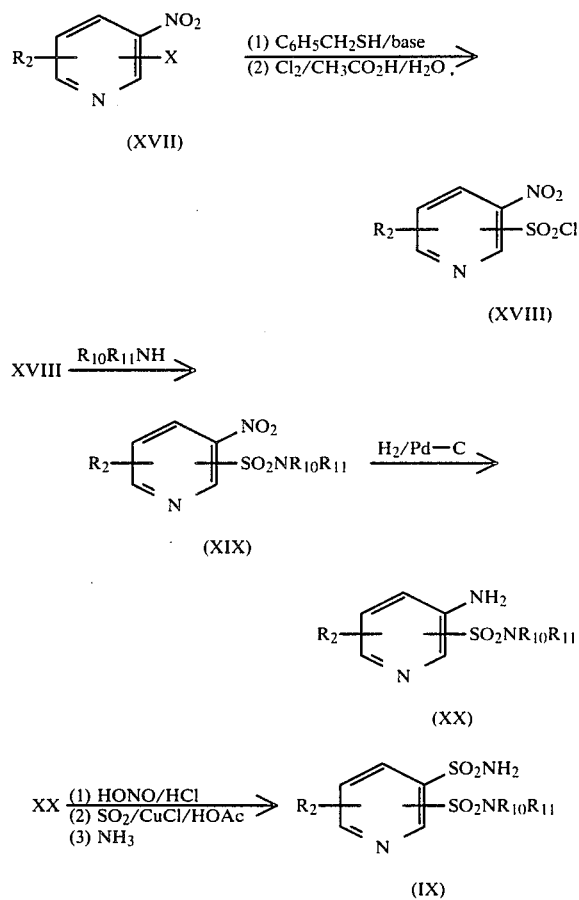

wherein R$_2$, R$_{10}$ and R$_{11}$ are as previously defined and X is Cl or Br.

Nucleophic displacement of halogen from 2- or 4-halo-3-nitropyridines of Formula XVII with benzyl mercaptan affords the 2- or 4-benzylthio-3-nitropyridines. Oxidation of benzylic sulfides to the corresponding sulfonyl chlorides, e.g., XVIII, with chlorine in aqueous acetic acid is taught by R. F. Langler, *Canad. J. Chem.*, 54, 498 (1956). Methods for conversion of sulfonyl chlorides of Formula XVIII to sulfonamides of Formula XIX are well known in the art.

Following reduction by conventional methods of the nitro group of compounds of Formula XIX, 3-aminopyridines of Formula XX are converted to the corresponding 3-pyridinesulfonylchlorides by the method disclosed by H. L. Yale and F. Sowinski, *J. Org. Chem.*, 25, 1824 (1960). Methods of converting the sulfonyl chlorides to the sulfonamides, such as those of Formula IX, are well known to the skilled artisan.

The compounds of this invention and their preparation are further illustrated by the following examples wherein temperatures are given in degrees centigrade.

EXAMPLE 1

2-Chloro-3-pyridinesulfonylisocyanate

To 125 ml of dry xylene was added with stirring 20.7 g of 2-chloro-N-(butylcarbamoyl)-3-pyridinesulfonamide. This solution was heated to reflux, and phosgene added until no further uptake of this gas was observed. It was then cooled, filtered and the solvent was removed in vacuo to yield 2-chloro-3-pyridinesulfonylisocyanate as an oil Bp 108°–110° (0.7 mm Hg). This product showed a sharp absorption peak in the infrared region at 2220 cm$^{-1}$.

By using the procedure of Example 1 with the appropriate N-(alkylcarbamoyl)pyridinesulfonamide, the sulfonyl isocyanate of Table 1 can be prepared. The pyridinesulfonylisothiocyanates of Table 1 are prepared according to the method of K. Dickere and E. Kühle as described in Equation 2.

TABLE I

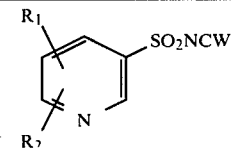

| R$_1$ | R$_2$ | W |
|---|---|---|
| 2-CH$_3$ | 6-CH$_3$ | S |
| 4-CO$_2$C$_2$H$_5$ | H | O |
| 2-CO$_2$CH$_3$ | H | O |
| 4-CO$_2$(iC$_3$H$_7$) | H | O |
| 4-OCH$_3$ | H | O |
| 4-Cl | H | O |
| 2-F | H | O |
| 2-Br | H | O |
| 4-SC$_4$H$_9$ | H | O |
| 2-SC$_2$H$_5$ | H | O |
| 4-Br | H | O |
| 4-N(CH$_3$)$_2$ | H | O |
| 4-SO$_2$N(CH$_3$)$_2$ | H | O |
| H | H | O |
| 2-CH$_3$ | H | O |
| 2-n-C$_4$H$_9$ | H | O |
| 4-CH$_2$CH$_3$ | H | S |
| 4-i-C$_3$H$_7$ | 5-Cl | O |
| 2-Cl | H | O |
| 4-Br | H | S |
| 4-F | H | O |
| 2-OCH$_3$ | 4-Cl | O |
| 4-O(n-C$_3$H$_7$) | H | S |
| 2-SCH$_3$ | H | O |
| 4-SCH$_2$CH$_3$ | 2-CH$_3$ | O |
| 2-N(CH$_3$)$_2$ | H | O |
| 4-N(CH$_3$)C$_2$H$_5$ | 6-CH$_3$ | O |
| 2-SO$_2$N(C$_2$H$_5$)$_2$ | H | O |
| 4-SO$_2$N(CH$_3$)$_2$ | 5-CH$_3$ | O |

TABLE I-continued

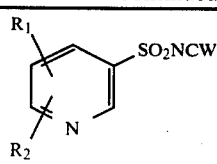

| R₁ | R₂ | W |
| --- | --- | --- |
| 2-CO₂CH₃ | 5-Br | O |
| 4-CO₂i-C₃H₇ | H | S |
| 2-Br | 6-Br | O |
| 4-Cl | 2-Cl | O |
| H | 6-CH₃ | S |
| 4-CH₃ | 2-Cl | O |
| H | 6-Cl | O |
| 4-n-C₄H₉ | H | S |
| 2-CO₂—i-C₃H₇ | H | O |
| 2-CO₂CH₃ | H | O |
| H | H | S |
| 2-Cl | H | S |
| 2-CO₂—i-C₃H₇ | H | S |
| 2-CO₂CH₃ | H | S |
| 2-CH₃ | H | S |
| H | H | S |
| 2-SO₂N(CH₂CH₃)₂ | 6-CH₃ | O |
| 2-N(CH₃)CH₂CH₃ | 6-Cl | O |
| 2-N(CH₃)₂ | 6-CH₃ | S |
| 2-N(CH₂CH₃)₂ | 6-Cl | O |
| 2-SO₂N(CH₃)CH₂CH₃ | 6-CH₃ | O |
| 4-SO₂N(CH₂CH₃)₂ | 2-CH₃ | O |

EXAMPLE 2

Methyl(4,6-dimethylpyrimidin-2-yl)carbamate

To 2-Amino-4,6-dimethylpyrimidine (10 g) dissolved in dimethylcarbonate (80 ml) was added sodium methoxide (4.4 g) and the mixture refluxed for four hours. The mixture was cooled and acetic acid (5 ml) was added. The mixture was then partitioned between water (100 ml) and methylene chloride (300 ml). A second methylene chloride extraction of the aqueous phase was made and the combined methylene chloride phase washed with water (50 ml) containing NH₄Cl. The solvent was evaporated and the residue triturated with a methylene chloride/1-chlorobutane mixture. The filtrate, on concentration and addition of hexane gave 6.7 g of the pure carbamate, m.p. 80°–85° C. IR: NH at 3200; carbonyl at 1745 cm⁻¹. NMR: 2.4 ppm, 2×CH₃, singlet; ArH 6.75 ppm 1H, singlet 8.9 ppm, NH, braod.

EXAMPLE 3

N-[(4,6-dimethylpyrimidin-2-yl)aminocarbonyl]-3-pyridinesulfonamide

To a slurry of 3-pyridinesulfonamide (1 m mole) in methylene chloride is added 2 m mole of trimethylaluminum. Following methane evolution, the reaction mixture becomes homogeneous, whereupon 1 m mole of methyl (4,6-dimethylpyrimidin-2-yl)carbamate is added, and stirring is continued for 66 hours. Aqueous acetic acid is added and the product is extracted into methylene chloride. The solvent is evaporated and the product is isolated by trituration on chromatography.

EXAMPLE 4

2-Chloro-N-[(4-methoxy-6-methylpyrimidin-2-yl)aminocarbonyl]-3-pyridinesulfonamide To a stirred suspension of 1.4 g of 2-amino-4-methoxy-6-methylpyrimidine in 20 ml of dry acetonitrile at room temperature was added 2.2 g of 2-chloropyridine-3-sulfonylisocyanate. The mixture was stirred for several hours and filtered. Evaporation of the filtrate yielded a solid residue which was stirred in approximately 30 ml of water while adjusting the pH of this mixture to 11 by the addition of 10% of NaOH. This solution was filtered, the filtrate pH adjusted to pH 7 by adding 10% hydrochloric acid and the resulting neutral solution was again filtered. The desired product was then precipitated from this filtrate by adjusting the pH to 2, collected in a sintered funnel and dried in a vacuum oven at room temperature. It melted at 165°–168°.

By using the procedure of Examples 2 and 3 with the appropriately substituted 2-aminopyrimidine and the appropriately substituted pyridine-3-sulfonamide, or the procedure of Example 4 with an equivalent amount of a 2-aminopyrimidine and appropriately substituted sulfonylisocyanate or isothiocyanate, the compounds of Table II can be prepared.

TABLE II

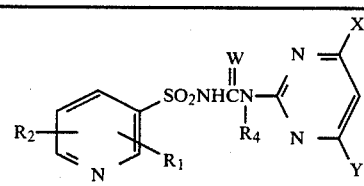

| R₁ | R₂ | R₄ | W | X | Y | m.p. |
| --- | --- | --- | --- | --- | --- | --- |
| H | H | H | O | CH₃ | CH₃ | 152° dec. |
| H | H | H | S | CH₃ | OCH₃ | |
| H | H | H | O | OCH₃ | OCH₃ | 176° dec. |
| 2-Cl | H | H | O | OCH₃ | OCH₃ | 160–165° |
| 2-Cl | H | H | O | CH₃ | CH₂OCH₃ | |
| 2-Cl | H | H | O | CH₃ | CH₃ | 140–145° |
| 2-Cl | H | H | S | CH₃ | SCH₃ | |
| 2-Cl | H | CH₃ | O | CH₃ | OCH₃ | |
| 2-CH₃ | 6-CH₃ | H | O | CH₃ | OCH₃ | |
| 4-CH₃ | H | CH₃ | O | CH₃ | OCH₂CH₂OCH₃ | |
| 2-nC₃H₇ | H | H | O | CH₃ | OCH₃ | |
| 4-C₂H₅ | 6-Cl | H | O | CH₃ | OCH(CH₃)CO₂CH₃ | |
| 4-Cl | H | H | O | CH₃ | N(CH₃)₂ | |
| 4-F | H | H | O | CH₃ | OCH₂CH₂CO₂C₂H₅ | |
| 4-Br | H | CH₃ | S | CH₃ | OCH₃ | |

TABLE II-continued $$\text{R}_2\text{-}\underset{\underset{\text{R}_1}{\mid}}{\overset{}{\text{pyridyl}}}\text{-SO}_2\text{NHC}(\text{W})\text{N}(\text{R}_4)\text{-triazinyl}(X,Y)$$

| R₁ | R₂ | R₄ | W | X | Y | m.p. |
|---|---|---|---|---|---|---|
| 2-Cl | 6-Cl | H | O | OCH₃ | OCH₃ | 182–185° |
| 2-Cl | 6-Cl | H | O | CH₃ | OCH₃ | 180–183° |
| 4-OCH₃ | H | H | O | CH₃ | OCH₃ | |
| 2-OC₂H₅ | H | H | O | OCH₃ | OCH₃ | |
| 4-SnC₃H₇ | H | H | O | CH₃ | CH₃ | |
| 2-SCH₃ | H | H | O | OCH₃ | OCH₃ | |
| 4-N(CH₃)₂ | H | H | O | CH₃ | CH₃ | |
| 2-N(CH₃)₂ | H | H | O | CH₃ | OCH₃ | |
| 2-N(CH₃)C₂H₅ | H | H | O | CH₃ | OCH₃ | |
| 2-SO₂N(CH₃)₂ | H | H | O | OCH₃ | CH₂OCH₃ | |
| 4-SO₂N(C₂H₅)₂ | H | H | S | CH₃ | CH₃ | |
| 2-CO₂CH₃ | 4-CH₃ | H | O | OCH₃ | OCH₃ | |
| 4-CO₂iC₃H₇ | H | CH₃ | O | CH₃ | OCH₃ | |
| 2-CO₂nC₄H₉ | 6-CH₃ | H | O | CH₃ | CH₃ | |
| 4-CO₂C₂H₅ | H | H | O | OCH₃ | OCH₃ | |
| 4-CO₂CH₃ | 5-Br | H | O | CH₃ | OCH₃ | |
| H | 6-Cl | H | O | OCH₃ | OCH₃ | 211–14° |
| 2-SO₂N(CH₂CH₃)₂ | H | H | O | OCH₃ | OCH₃ | |
| 2-N(CH₃)CH₂CH₃ | 6-Cl | H | O | CH₃ | CH₃ | |
| 2-N(CH₃)CH₂CH₃ | 6-Cl | H | O | CH₃ | OCH₃ | |
| 2-N(CH₃)CH₂CH₃ | 6-Cl | H | O | OCH₃ | OCH₃ | |
| 2-N(CH₃)₂ | 6-CH₃ | H | S | CH₃ | CH₃ | |
| 2-N(CH₃)₂ | 6-CH₃ | H | S | CH₃ | OCH₃ | |
| 2-N(CH₃)₂ | 6-CH₃ | H | S | OCH₃ | OCH₃ | |
| 2-N(CH₂CH₃)₂ | H | H | O | CH₃ | CH₃ | |
| 2-N(CH₂CH₃)₂ | 6-Cl | H | O | CH₃ | OCH₃ | |
| 2-N(CH₂CH₃)₂ | 6-Cl | H | O | OCH₃ | OCH₃ | |
| 2-SO₂N(CH₃)CH₂CH₃ | 6-CH₃ | H | O | CH₃ | CH₃ | |
| 2-SO₂N(CH₃)CH₂CH₃ | H | H | O | CH₃ | OCH₃ | |
| 2-SO₂N(CH₃)CH₂CH₃ | 6-CH₃ | H | O | OCH₃ | OCH₃ | |
| 4-SO₂N(CH₂CH₃)₂ | H | H | O | CH₃ | CH₃ | |
| 4-SO₂N(CH₂CH₃)₂ | H | H | O | CH₃ | OCH₃ | |
| 4-SO₂N(CH₂CH₃) | H | H | O | OCH₃ | OCH₃ | |

EXAMPLE 5

2-Chloro-N-[(4-methoxy-6-methyl-1,3,5-triazin-2-yl)aminocarbonyl]-3-pyridinesulfonamide To a stirred suspension of 1.4 g of 2-amino-4-methoxy-6-methyltriazine in 20 ml of dry acetonitrile at room temperature was added 2.2 g of 2-chloropyridine-3-sulfonylisocyanate. The mixture was stirred for several hours and then evaporated to dryness. The residue was mixed with 30 ml of water and enough 10% sodium hydroxide to adjust the pH to 11. This mixture was filtered and the filtrate adjusted to pH7 by the addition of 10% hydrochloric acid and then refiltered. Acidification of this filtrate to pH2 caused the desired compound to precipitate. The desired compound was filtered off and after drying in a vacuum oven was found to melt at 160°–165°.

EXAMPLE 6

N-[(4,6-Dimethoxy-1,3,5-triazin-2-yl)aminothioxomethyl]-3-pyridinesulfonamide

A mixture of 1.58 g of 3-pyridinesulfonamide, 2.04 g of 4,6-dimethoxy-2-isothiocyanato-1,3-5-triazine and 1.5 g of anhydrous potassium carbonate was stirred in 75 ml of acetone for 60 hours at ambient temperature. The reaction mixture was then poured into 500 ml of cold water, acidified with hydrochloric acid and the precipitated product was removed by filtration to yield 2.7 g of the desired compound, m.p. 158°–160°.

EXAMPLE 7

N-[(4,6-Dimethoxy-1,3,5-triazin-2-yl)aminocarbonyl]-3-pyridinesulfonamide

A mixture containing 2.7 g of N-[(4,6-dimethoxy-1,3,5-triazin-2-yl)aminothioxomethyl]-3-pyridinesulfonamide, 2.98 g of mercuric oxide and 75 ml of acetone was stirred at ambient temperature for 60 hours and then filtered. Evaporation of the filtrate in vacuo yielded the desired product as a residual white solid of m.p. 182°–185° dec.

By using the procedure of Examples 2 and 3, or by using the procedure of Example 5 with an equivalent amount of a 2-amino-1,3,5-triazine and appropriately substituted sulfonylisocyanate or isothiocyanate, the compounds of Table III can be prepared. Alternatively, N-(aminothioxomethyl)pyridinesulfonamides of Table III can be prepared according to the method of Example 4 by substituting equivalent amounts of an appropriately substituted pyridinesulfonamide and isothiocyanato-1,3,5-triazine. The aminothioxomethylsulfonamides obtained by the method of Example 6 or by Equations 3 or 5 wherein W=S can also be converted to the N-(aminocarbonyl)pyridinesulfonamides of Table III by reaction with mercuric oxide according to the procedure of Example 7.

TABLE III

| R₁ | R₂ | R₄ | W | X | Y | m.p. |
|---|---|---|---|---|---|---|
| 2-Cl | H | H | S | $CH_3$ | $SCH_3$ | |
| 2-Cl | H | $CH_3$ | O | $CH_3$ | $OCH_3$ | |
| 2-$CH_3$ | 6-$CH_3$ | H | O | $CH_3$ | $OCH_3$ | |
| 4-$CH_3$ | H | $CH_3$ | O | $CH_3$ | $OCH_2CH_2OCH_3$ | |
| 2-Cl | H | $CH_3$ | O | $OCH_3$ | $OCH_3$ | 115–122° |
| 2-$CO_2CH_2CH_2Cl$ | H | H | O | $CH_3$ | $OCH_3$ | |
| 2-$CO_2CH_2$—CH=$CH_2$ | H | H | O | $CH_3$ | $OCH_3$ | |
| 2-$CO_2CH_2CH_2OCH_3$ | H | H | O | $OCH_3$ | $OCH_3$ | |
| 2-$CH_3$ | H | $CH_3$ | O | $CH_3$ | $OCH_2CH_2CH_2OCH_3$ | |
| 2-$CH_3$ | H | H | O | $CH_3$ | $OCH_2CO_2CH_3$ | |
| 4-$C_2H_5$ | 2-$CH_3$ | H | O | $CH_3$ | $OCH_2CO_2C_2H_5$ | |
| 4-n-$C_4H_9$ | 2-$CH_3$ | H | S | $CH_3$ | $OCH(CH_3)CO_2C_2H_5$ | |
| 4-Br | 5-Cl | H | O | $CH_3$ | $SCH_2CO_2CH_3$ | |
| 2-$CO_2CH_3$ | H | H | O | $CH_3$ | $S(CH_2)_2CO_2C_2H_5$ | |
| 4-$CO_2C_2H_5$ | H | H | O | $OCH_3$ | $OCH_3$ | |
| 4-$CO_2$—i-$C_3H_7$ | H | $CH_3$ | S | $CH_3$ | $OCH_3$ | |
| 6-$CO_2CH_3$ | H | H | O | $CH_3$ | $OCH_3$ | |
| 4-$OCH_3$ | H | H | O | $CH_3$ | $OCH_3$ | |
| 2-$OCH_3$ | H | H | O | $OC_2H_5$ | $OCH_3$ | |
| 4-$CH_3$ | 6-Cl | H | O | $CH_3$ | $CF_3$ | |
| 4-Cl | H | H | O | $CH_3$ | $N(CH_3)_2$ | |
| 2-F | H | H | S | $CH_3$ | Cl | |
| 2-Br | H | H | O | $CH_3$ | Cl | |
| 4-$OC_2H_5$ | H | H | O | $CH_3$ | $SC_2H_5$ | |
| 4-$SC_2H_5$ | H | $CH_3$ | S | $CH_3$ | $S(CH_2)_2OC_2H_5$ | |
| 4-S—n$C_4H_9$ | H | H | O | $OCH_3$ | $OCH_3$ | |
| 2-$SC_2H_5$ | H | H | O | $CH_3$ | $OCH_3$ | |
| 4-F | H | H | O | $CH_3$ | $OCH_2CH_2CO_2C_2H_5$ | |
| 4-Br | H | $CH_3$ | S | $CH_3$ | $OCH_3$ | |
| 2-$SCH_3$ | H | H | O | $CH_3$ | $OCH_3$ | |
| Br | H | H | O | $OCH_3$ | $OCH_3$ | |
| 4-n-$C_4H_9$ | H | H | S | $CH_3$ | $SCH_2CO_2CH_3$ | |
| 4-n-$C_4H_9$ | H | H | O | $OCH_3$ | $OCH_3$ | |
| 4-F | 6-Cl | H | O | $OC_2H_5$ | $CH_2OCH_3$ | |
| 2-Cl | 6-Cl | H | S | $OCH_3$ | $OCH_3$ | 143–145° |
| 2-Cl | 6-Cl | H | O | $CH_3$ | $OCH_3$ | 93–96° |
| 2-Cl | 6-Cl | H | O | $OCH_3$ | $OCH_3$ | 172–177° |
| H | H | H | O | $CH_3$ | $CH_3$ | |
| H | H | H | S | $CH_3$ | $OCH_3$ | |
| H | H | H | O | $OCH_3$ | $OCH_3$ | 230° dec. |
| 2-Cl | H | H | O | $OCH_3$ | $OCH_3$ | 144–150° |
| 2-Cl | H | H | O | $CH_3$ | $CH_2OCH_3$ | |
| 2-Cl | H | H | O | $CH_3$ | $CH_3$ | 155–158° |
| 2-$CO_2CH_3$ | H | H | O | $OCH_3$ | OCH | |
| 2-$CO_2CH_3$ | H | H | O | $CH_3$ | $OCH_3$ | |
| 2-$CO_2CH_3$ | H | H | O | $CH_3$ | $CH_3$ | |
| 2-$CO_2$—i-$C_3H_7$ | H | H | O | $CH_3$ | $CH_3$ | |
| 2-$CO_2$—i-$C_3H_7$ | H | H | O | $CH_3$ | $OCH_3$ | |
| 2-$CO_2$—i-$C_3H_7$ | H | H | O | $OCH_3$ | $OCH_3$ | |
| 4-$CH_3$ | H | H | S | $CH_3$ | $OCH_3$ | |
| 4-$CH_3$ | H | H | O | $CH_3$ | $CH_3$ | |
| 4-$CH_3$ | H | H | O | $OCH_3$ | $OCH_3$ | |
| 2-$CH_3$ | H | H | O | $OCH_3$ | $OCH_3$ | |
| 2-$CH_3$ | H | H | O | $CH_3$ | $OCH_3$ | |
| 2-$CH_3$ | H | H | O | $CH_3$ | $CH_3$ | |
| 4-Cl | H | H | O | $CH_3$ | $CH_3$ | |
| 4-Cl | H | H | S | $CH_3$ | $OCH_3$ | |
| 4-Cl | H | H | O | $OCH_3$ | $OCH_3$ | |
| 4-$CO_2CH_3$ | H | H | O | $CH_3$ | $CH_3$ | |
| 4-$CO_2CH_3$ | H | H | O | $CH_3$ | $OCH_3$ | |
| 4-$CO_2CH_3$ | H | H | O | $OCH_3$ | $OCH_3$ | |
| 4-$CO_2$—i-$C_3H_7$ | H | H | O | $CH_3$ | $CH_3$ | |
| 4-$CO_2$—i-$C_3H_7$ | H | H | O | $CH_3$ | $OCH_3$ | |
| 4-$CO_2$—i-$C_3H_7$ | H | H | O | $OCH_3$ | $OCH_3$ | |
| 4-$N(CH_3)_2$ | H | H | O | $CH_3$ | $CH_3$ | |
| 4-$N(CH_3)_2$ | H | H | O | $CH_3$ | $OCH_3$ | |
| 4-$N(CH_3)_2$ | H | H | O | $OCH_3$ | $OCH_3$ | |
| 4-$SO_2N(CH_3)_2$ | H | H | O | $CH_3$ | $CH_3$ | |
| 4-$SO_2N(CH_3)_2$ | H | H | O | $CH_3$ | $OCH_3$ | |

TABLE III-continued $$R_1\text{-Ar}(R_2)(N)\text{-SO}_2\text{NHC}(W)\text{N}(R_4)\text{-Ar}(N,N)(X)(Y)$$

| R₁ | R₂ | R₄ | W | X | Y | m.p. |
|---|---|---|---|---|---|---|
| 4-SO₂N(CH₃)₂ | H | H | O | OCH₃ | OCH₃ | |
| 2-SO₂N(CH₂CH₃)₂ | H | H | O | CH₃ | CH₃ | |
| 2-SO₂N(CH₂CH₃)₂ | H | H | O | CH₃ | OCH₃ | |

By using the procedure of Examples 4 or 5 with an equivalent amount of a 3-amino-1,2,4-triazine and appropriately substituted sulfonylisocyanate or isothiocyanate, the compounds of Table IV can be prepared.

TABLE IV

| R₁ | R₂ | W | Y₁ | X₁ |
|---|---|---|---|---|
| 2-Cl | H | O | CH₃ | OCH₃ |
| 2-Cl | H | O | CH₃ | OCH₃ |
| 2-Cl | H | S | OCH₃ | OCH₃ |
| 4-C₂H₅ | 2-CH₃ | O | CH₃ | CH₃ |
| 4-Br | 6-Cl | O | CH₃ | OCH₃ |
| 4-CO₂C₂H₅ | H | O | CH₃ | CH₃ |
| 2-CO₂CH₃ | H | O | CH₃ | CH₃ |
| 2-OCH₃ | H | O | CH₃ | CH₃ |
| 2-F | H | S | CH₃ | CH₃ |
| 2-Br | H | O | OCH₃ | OCH₃ |
| 6-SC₂H₅ | H | S | OCH₃ | CH₃ |
| 4-F | H | S | OCH₃ | CH₃ |
| 2-Cl | H | O | H | CH₃ |
| 2-Cl | H | O | CH₃ | OCH₂CH₂ |
| 2-N(CH₃)₂ | H | O | CH₃ | OCH₃ |
| 4-SO₂N(CH₃)₂ | H | O | OCH₃ | OCH₃ |

By using the procedure of Examples 4 or 5 with an equivalent amount of the appropriate 4-aminopyrimidines and appropriately substituted sulfonylisocyanate or isothiocyanate, the compounds of Table V can be prepared.

TABLE V

| R₁ | R₂ | W | Y₁ | X₁ |
|---|---|---|---|---|
| 2-C₂H₅ | H | O | OCH₃ | OCH₃ |
| 4-n-C₄H₉ | H | S | OCH₃ | CH₃ |
| 4-F | H | O | OCH₃ | C₂H₅ |
| 4-SC₂H₅ | H | S | OCH₃ | OCH₃ |
| 2-Br | H | O | CH₃ | Cl |
| 4-F | H | O | CH₃ | OCH₂CH₃ |
| 2-OCH₃ | H | O | OCH₃ | H |
| 2-CO₂CH₃ | H | O | CH₃ | OCH₂CH₃ |
| 2-SO₂NCH₂CH₃ | H | O | OCH₃ | CH₃ |
| 2-N(CH₃)₂ | 6-CH₃ | O | OCH₃ | OCH₃ |
| 4-CO₂CH₃ | H | O | OCH₃ | Cl |
| 4-CO₂C₂H₅ | H | O | OCH₃ | OCH₃ |

TABLE V-continued

| R₁ | R₂ | W | Y₁ | X₁ |
|---|---|---|---|---|
| 2-Br | 6-Cl | S | OCH₃ | H |
| 4-C₂H₅ | 2-CH₃ | O | OCH₃ | Cl |
| 2-Cl | H | O | OCH₃ | OC₂H₅ |
| 2-Cl | H | O | OCH₃ | CH₃ |
| 2-Cl | H | S | OCH₃ | Cl |

By using an appropriate N-[(triazinyl)aminocarbonyl]pyridinesulfonamide or N[(pyrimidinyl)aminocarbonyl]pyridinesulfonamide, the compounds of Formula I (where R₃=CH₃) set forth in Table VI can be prepared. For example, the compound of Example 4 can be converted to N-[(4-methoxy-6-methyl-1,3,5-triazin-2-yl)aminocarbonyl]-2-chloro-N-methyl-3-pyridinesulfonamide by the methylation reaction set forth in Equation 3 as follows: An equivalent amount of sodium hydride (50% mineral oil dispersion) can be added to a solution of the compound of Example 4 in dimethylformamide under a nitrogen atmosphere. After hydrogen evolution has ceased, an equivalent amount of dimethylsulfate can be added. The resulting reaction mixture can be stirred for 2-18 hours and the reaction mixture can then be poured into a large volume of water to form a precipitate which can be filtered to yield the aboveidentified product.

TABLE VI

| R₁ | R₂ | R₄ | W | X | Y | Z |
|---|---|---|---|---|---|---|
| 2-Cl | H | H | OCH₃ | OCH₃ | OCH₃ | CH |
| 2-Cl | H | H | CH₃ | OCH₃ | OCH₃ | N |
| 2-Cl | H | CH₃ | CH₃ | OCH₃ | OCH₃ | CH |
| 2-Cl | H | H | CH₃ | OCH₃ | OCH₃ | CH |
| 2-CO₂CH₃ | H | H | CH₃ | OCH₃ | N(CH₃)₂ | CH |
| 2-CO₂CH₃ | H | H | CH₃ | OCH₃ | N(CH₃)₂ | N |
| 2-CO₂C₂H₅ | H | H | CH₃ | OCH₃ | OCH₂CH₂OCH₃ | CH |
| 4-CO—n-C₄H₉ | H | CH₃ | CH₃ | OCH₃ | CH₂OCH₃ | N |
| 4-CH₃ | 6-Cl | H | CH₃ | OCH₃ | N(CH₃)₂ | N |
| 4-CH₃ | 6-Cl | CH₃ | CH₃ | OCH₃ | SC₂H₅ | CH |

TABLE VIII

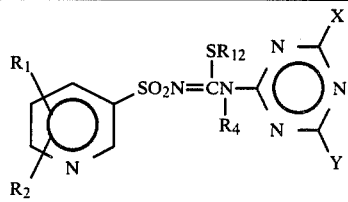

| R₁ | R₂ | R₄ | X | Y | R₁₂ |
|---|---|---|---|---|---|
| 2-Cl | H | CH₃ | CH₃ | OCH₃ | CH₂CH₂CH₃ |
| 2-Cl | H | H | CH₃ | OCH₃ | CH₃ |
| 2-CH₃ | 6-CH₃ | H | CH₃ | OCH₃ | CH₃ |
| 4-CH₃ | H | CH₃ | CH₃ | OCH₂CH₂OCH₃ | CH₃ |
| 2-CO₂CH₂CH₂Cl | H | H | CH₃ | OCH₃ | CH₃ |
| 2-CO₂CH₂CH=CH₂ | H | H | CH₃ | OCH₃ | CH₃ |
| 2-CO₂CH₂CH₂OCH₃ | H | H | OCH₃ | OCH₃ | CH₃ |
| 2-CH₃ | H | CH₃ | CH₃ | OCH₂CH₂CH₂OCH₃ | CH₃ |
| 2-CH₃ | H | H | CH₃ | OCH₂CO₂CH₃ | CH₃ |
| 4-C₂H₅ | 2-CH₃ | H | CH₃ | OCH₂CO₂C₂H₅ | CH₃ |
| 4-Br | 6-Cl | H | CH₃ | SCH₂CO₂CH₃ | CH₃ |
| 2-CO₂CH₃ | H | H | CH₃ | S(CH₂)₂CO₂C₂H₅ | CH₃ |
| 4-CO₂C₂H₅ | H | H | OCH₃ | OCH₃ | CH₃ |
| 2-CO₂CH₃ | H | H | CH₃ | OCH₃ | CH(CH₃)₂ |
| 4-OCH₃ | H | H | CH₃ | OCH₃ | CH₃ |
| 2-OCH₃ | H | H | OC₂H₅ | OCH₃ | CH₃ |
| 4-CH₃ | 2-Cl | H | CH₃ | CF₃ | CH₃ |
| 4-Cl | H | H | CH₃ | N(CH₃)₂ | CH₃ |
| 2-Br | H | H | CH₃ | Cl | CH₃ |
| 2-OC₂H₅ | H | H | CH₃ | SC₂H₅ | CH₃ |
| 4-S—n-C₄H₉ | H | H | OCH₃ | OCH₃ | CH₃ |
| 2-SC₂H₅ | H | H | CH₃ | OCH₃ | C₄H₉ |
| 4-F | H | H | CH₃ | OCH₂CH₂CO₂C₂H₅ | CH₃ |
| —H | H | H | CH₃ | CH₃ | CH₂₂ |
| —H | H | H | OCH₃ | OCH₃ | CH₃ |
| 2-Cl | H | H | OCH₃ | OCH₃ | CH₃ |
| 2-Cl | H | H | CH₃ | CH₂OCH₃ | CH₃ |
| 2-Cl | H | H | CH₃ | CH₃ | CH₃ |
| 2-CO₂CH₃ | H | H | OCH₃ | OCH | CH₃ |
| 2-CO₂CH₃ | H | H | CH₃ | OCH₃ | CH₃ |
| 2-CO₂CH₃ | H | H | CH₃ | CH₃ | CH₃ |
| 2-CO₂—i-C₃H₇ | H | H | CH₃ | CH₃ | CH₃ |
| 2-CO₂—i-C₃H₇ | H | H | CH₃ | OCH₃ | CH₃ |
| 2-CO₂—i-C₃H₇ | H | H | OCH₃ | OCH₃ | CH₃ |
| 2-CH₃ | H | H | OCH₃ | OCH₃ | CH₃ |
| 2-CH₃ | H | H | CH₃ | OCH₃ | CH₃ |
| 2-CH₃ | H | H | CH₃ | CH₃ | CH₃ |
| 4-Cl | H | H | CH₃ | CH₃ | CH₃ |
| 4-Cl | H | H | OCH₃ | OCH₃ | CH₃ |
| 4-CO₂CH₃ | H | H | CH₃ | CH₃ | CH₃ |
| 4-CO₂CH₃ | H | H | CH₃ | OCH₃ | CH₃ |
| 4-CO₂CH₃ | H | H | OCH₃ | OCH₃ | CH₃ |
| 4-CO₂—i-C₃H₇ | H | H | CH₃ | CH₃ | CH₃ |
| 4-CO₂—i-C₃H₇ | H | H | OCH₃ | OCH₃ | CH₃ |
| 4-CO₂—i-C₃H₇ | H | H | CH₃ | OCH₃ | CH₃ |
| 4-CH₃ | H | H | CH₃ | CH₃ | CH₃ |
| 4-CH₃ | H | H | OCH₃ | OCH₃ | CH₂CH₂CH₃ |
| 4-N(CH₃)₂ | H | H | CH₃ | CH₃ | CH₃ |
| 4-SO₂N(CH₃)₂ | H | H | CH₃ | OCH₃ | CH₂CH₃ |
| 2-SO₂N(CH₂CH₃) | H | H | OCH₃ | OCH₃ | CH₃ |
| 2-SO₂N(CH₂)CH₂CH₃ | 6-CH₃ | H | CH₃ | OCH₃ | CH₃ |

TABLE IX

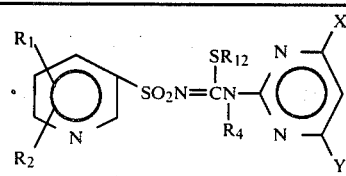

| R₁ | R₂ | R₄ | X | Y | R₁₂ |
|---|---|---|---|---|---|
| 4-C₂H₅ | H | H | CH₃ | CF₃ | CH₃ |
| 2-Cl | H | CH₃ | CH₃ | OCH₃ | CH₃ |
| 2-CH₃ | 6-CH₃ | H | CH₃ | OCH₃ | CH₃ |
| 4-CH₃ | H | CH₃ | CH₃ | OCH₂CH₂OCH₃ | CH₃ |
| 2-CO₂CH₂CH=CH₂ | H | H | CH₃ | OCH₃ | CH₃ |

TABLE VI-continued

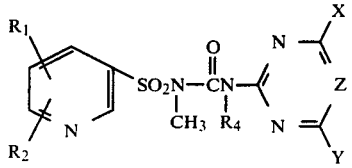

| R₁ | R₂ | R₄ | W | X | Y | Z |
|---|---|---|---|---|---|---|
| 2-CH₃ | 6-Cl | H | CH₃ | OCH₃ | | N |
| 2-Br | H | H | CH₃ | OCH₂CO₂C₂H₅ | | CH |
| 2-SO₂NH(CH₃)CH₂CH₃ | 6-CH₃ | H | OCH₃ | OCH₃ | | CH |
| 4-SO₂N(CH₂CH₃)₂ | H | H | CH₃ | OCH₃ | | N |
| 2-N(CH₂CH₃)₂ | 6-Cl | H | CH₃ | CH₃ | | CH |
| 4-N(CH₃)₂ | H | H | CH₃ | OCH₃ | | N |
| 2-F | 6-Cl | H | CH₃ | CF₃ | | CH |
| 4-F | 6-Cl | H | CH₃ | OC₂H₅ | | N |

EXAMPLE 8

N-(3-Pyridinylsulfonyl)carbonimidodithioic acid, dimethyl ester

To a stirred solution of 15.8 g of pyridine-3-sulfonamide in 70 ml of N,N-dimethylformamide was added 6.6 g of powdered potassium hydroxide. The mixture was stirred for 50 minutes at room temperature and 3 ml of carbon disulfide was added dropwise. The solution was then stirred at room temperature for 0.5 hr., then 3.3 g of powdered potassium hydroxide and 1.5 ml of carbon disulfide was added. The mixture was stirred for 0.5 hr., then 3.3 g of powdered potassium hydroxide and 1.5 ml of carbon disulfide was added. The mixture was stirred for 0.5 hr. again, and cooled at 0°–5° C., then 13 ml of iodomethane was added dropwise. The resulting mixture was stirred overnight and poured onto 250 g of ice-water. The precipitate was filtered and rinsed with water until neutral, then dried at reduced pressure to give 17 g of pale yellow solid, m.p. 115°–118° C.

Using the method described in Example 8, the compounds of Table VII can be prepared from the appropriately substituted pyridinesulfonamide and the appropriate alkylating agent.

TABLE VII

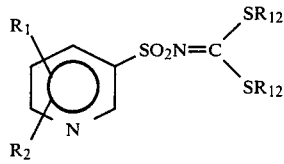

| R₁ | R₂ | R₁₂ |
|---|---|---|
| 2-Cl | H | CH₃ |
| 2-CH₃ | 6-CH₃ | CH₃ |
| 2-CH₃ | H | CH₃ |
| 4-CH₃ | H | CH₃ |
| 4-C₂H₅ | 2-CH₃ | CH₃ |
| 4-n-C₄H₉ | 2-CH₃ | CH₃ |
| 2-Cl | 6-Cl | CH₃ |
| 4-CO₂C₂H₅ | H | CH₃ |
| 2-CO₂—i-C₃H₇ | H | CH₃ |
| 4-OCH₃ | H | CH₃ |
| 2-n-C₄H₉ | H | CH₃ |
| 4-CH₃ | 6-Cl | CH₂CH₂CH₃ |
| 4-Cl | H | CH₃ |

TABLE VII-continued

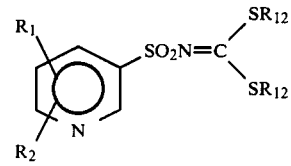

| R₁ | R₂ | R₁₂ |
|---|---|---|
| 2-F | H | CH₃ |
| 4-Br | H | CH₃ |
| 4-SC₂H₅ | H | CH₃ |
| 2-SC₄H₉ | H | CH₃ |
| 2-SC₂H₅ | H | CH₃ |
| 4-F | H | CH₃ |
| 4-Br | H | CH₃ |
| 2-SCH₃ | H | CH₃ |
| 2-Br | H | CH(CH₃)₂ |
| 4-n-C₄H₉ | H | CH₃ |
| 6-n-C₄H₉ | H | CH₃ |
| 4-F | 6-Cl | CH₃ |
| H | H | CH₂CH₂CH₃ |
| 2-Cl | 4-Cl | CH₂CH₂CH₃ |
| 2-CO₂—i-C₃H₇ | H | CH₂CH₂CH₃ |
| 2-CO₂CH₃ | H | CH₂CH₂CH₃ |
| H | H | CH₂CH₂CH₃ |
| 2-Cl | H | CH₂CH₂CH₃ |
| 2-CO₂—i-C₃H₇ | H | CH₂CH₂CH₃ |
| 2-CO₂CH₃ | H | CH₂CH₂CH₃ |
| 2-CH₃ | H | CH₂CH₂CH₃ |
| 2-CH₃ | H | CH₂CH₂CH₃ |
| H | H | CH₂CH₃ |
| H | H | CH₂CH₂CH₂CH₃ |
| 4-Cl | H | CH₃ |
| 4-NO₂ | H | CH₃ |
| 4-NO₂ | H | CH₃ |
| 4-CH₃ | H | CH₃ |
| 4-CH₃ | H | CH₃ |
| 4-CO₂CH₃ | H | CH₃ |
| 4-CO₂CH₃ | H | CH₂CH₂CH₂CH₃ |
| 4-CO₂—i-C₃H₇ | H | CH₃ |
| 4-SO₂N(CH₂CH₃)₂ | 2-CH₃ | CH₃ |
| 2-N(CH₃)₂ | 6-CH₃ | CH₂CH₃ |
| 4-N(CH₃)₂ | H | CH₃ |
| 4-SO₂N(CH₃)₂ | H | CH₂CH₂CH₂CH₃ |

EXAMPLE 9

N-(4-Methoxy-6-methyl-1,3,5-triazin-2-yl)-N'-(3-pyridinylsulfonyl)carbamimidothioic acid, methyl ester To a suspension of 0.9 g of sodium hydride (50% oil dispersion) in 25 ml of dry N,N-dimethylformamide was added 2.3 g of 2-amino-4,6-dimethoxypyrimidine. The resulting yellow suspension was stirred at room temperature for 3 hrs., then added to 3.95 g of 3-pyridinylsulfonylcarbonimidodithioic acid, dimethyl ester. The reddish slurry was stirred at room temperature for 2 hours, poured into 250 g of icewater and filtered to remove 1.6 g of unreacted, carbonimidodithioic acid, dimethyl ester. The filtrate was adjusted to pH 4 by adding 10% hydrochloric acid and the precipitate was filtered off, rinsed with water until neutral and then dried invacuo to give 2.6 g of the desired compound, m.p. 146°–149° C.

By using the procedure of Example 9 with an equivalent amount of an appropriate aminopyrimidine, or aminotriazine and an appropriately substituted pyridinylsulfonylcarbonimidodithioic acid, dialkyl ester, the compounds of Tables VIII, IX, X and XI can be prepared.

boron-trifluoride etherate. The mixture was stirred for 20 minutes, and then 0.4 g of N-(4-methoxy-6-methyl-1,3,5-triazin-2-yl)N'-(3-pyridinylsulfonyl)carbamimidothioic acid, methyl ester was added. The slurry was stirred at room temperature for 1 hour, filtered and the solid was washed with 50 ml of water, followed by 40 ml of dichloromethane, and dissolved with 25 ml of 0.1N sodium hydroxide. The basic solution was filtered and the filtrate acidified with dilute hydrochloric acid to yield the desired product as a precipitate. The solid was filtered off, washed with water, and dried to give 0.2 g of pale yellow solid, m.p. 185°–190° C.

EXAMPLE 11

N-[(4-methoxy-6-methyl-1,3,5-triazin-2-yl)aminocarbonyl]-3-pyridinesulfonamide

To 25 ml of 80% aqueous acetonitrile was added with stirring 0.6 g of mercuric chloride and then 0.34 g of N-(4-methoxy-6-methyl-1,3,5-triazin-2-yl)-N'-(3-pyridinylsulfonyl)carbamimidothioic acid, methyl ester. To this mixture, 0.22 g of calcium carbonate was added to adjust the pH to 7. The resulting mixture was heated to reflux for 2 hours, then cooled to room temperature and filtered. The solid was rinsed with 25 ml of dichloromethane three times, 25 ml of water three times, and then dissolved in 30 ml of 0.1N of sodium hydroxide. Acidification of the basic solution with dilute hydrochloric acid yielded the desired product as a precipitate which was filtered off, rinsed with water, and dried at reduced pressure to give 0.2 g of pale yellow solid, m.p. 185°–190° C.

By using the procedures of Examples 10 or 11, the compounds of Table XII can be prepared from the appropriately substituted pyridinesulfonyl carbamimidothioic acid esters.

TABLE XII

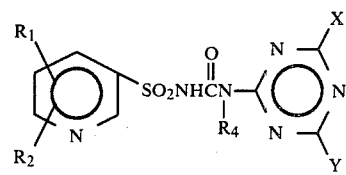

| $R_1$ | $R_2$ | $R_4$ | X | Y |
|---|---|---|---|---|
| 2-Cl | H | $CH_3$ | $CH_3$ | $OCH_3$ |
| 2-$CH_3$ | 6-$CH_3$ | H | $CH_3$ | $OCH_3$ |
| 4-$CH_3$ | H | $CH_3$ | $CH_3$ | $OCH_2CH_2OCH_3$ |
| 2-$CO_2CH_2CH_2Cl$ | H | H | $CH_3$ | $OCH_3$ |
| 2-$CO_2CH_2CH=CH_2$ | H | H | $CH_3$ | $OCH_3$ |
| 2-$CO_2CH_2CH_2OCH_3$ | H | H | $OCH_3$ | $OCH_3$ |
| 2-$CO_2CH_3$ | H | H | $CH_3$ | $S(CH_2)_2CO_2C_2H_5$ |
| 4-$CO_2C_2H_5$ | H | H | $OCH_3$ | $OCH_3$ |
| 2-$CO_2CH_3$ | H | H | $CH_3$ | $OCH_3$ |
| 4-$OCH_3$ | H | H | $CH_3$ | $OCH_3$ |
| 4-Cl | H | H | $CH_3$ | $N(CH_3)_2$ |
| 2-Br | H | H | $CH_3$ | Cl |
| 2-$OC_2H_5$ | H | H | $CH_3$ | $SC_2H_5$ |

TABLE XII-continued

| $R_1$ | $R_2$ | $R_4$ | X | Y |
|---|---|---|---|---|
| 4-S—n-$C_4H_9$ | H | H | $OCH_3$ | $OCH_3$ |
| 2-$SC_2H_5$ | H | H | $CH_3$ | $OCH_3$ |
| 4-F | H | H | $CH_3$ | $OCH_2CH_2CO_2C_2H_5$ |
| 2-$SCH_3$ | H | H | $CH_3$ | $OCH_3$ |
| 4-Br | H | H | $OCH_3$ | $OCH_3$ |
| 2-n-$C_4H_9$ | H | H | $OCH_3$ | $OCH_3$ |
| 2-F | 6-Cl | H | $OC_2H_5$ | $CH_2OCH_3$ |
| 2-Cl | H | H | $OCH_3$ | $OCH_3$ |
| 2-Cl | H | H | $CH_3$ | $CH_2OCH_3$ |
| 2-Cl | H | H | $CH_3$ | $CH_3$ |
| H | H | H | $CH_3$ | $CH_3$ |
| H | H | H | $OCH_3$ | $OCH_3$ |
| 2-$CO_2CH_3$ | H | H | $OCH_3$ | OCH |
| 2-$CO_2CH_3$ | H | H | $CH_3$ | $OCH_3$ |
| 2-$CO_2CH_3$ | H | H | $CH_3$ | $CH_3$ |
| 2-$CO_2$—i-$C_3H_7$ | H | H | $CH_3$ | $CH_3$ |
| 2-$CO_2$—i-$C_3H_7$ | H | H | $CH_3$ | $OCH_3$ |
| 2-$CO_2$—i-$C_3H_7$ | H | H | $OCH_3$ | $OCH_3$ |
| 2-$CH_3$ | H | H | $OCH_3$ | $OCH_3$ |
| 2-$CH_3$ | H | H | $CH_3$ | $OCH_3$ |
| 2-$CH_3$ | H | H | $CH_3$ | $CH_3$ |
| 4-Cl | H | H | $CH_3$ | $CH_3$ |
| 4-Cl | H | H | $OCH_3$ | $OCH_3$ |
| 4-$CO_2CH_3$ | H | H | $CH_3$ | $CH_3$ |
| 4-$CO_2CH_3$ | H | H | $CH_3$ | $OCH_3$ |
| 4-$CO_2CH_3$ | H | H | $OCH_3$ | $OCH_3$ |
| 4-$CO_2$—i-$C_3H_7$ | H | H | $CH_3$ | $CH_3$ |
| 4-$CO_2$—i-$C_3H_7$ | H | H | $OCH_3$ | $OCH_3$ |
| 4-$CO_2$—i-$C_3H_7$ | H | H | $OCH_3$ | $OCH_3$ |
| 4-$CH_3$ | H | H | $CH_3$ | $CH_3$ |
| 4-$CH_3$ | H | H | $OCH_3$ | $OCH_3$ |
| 2-$SO_2N(CH_3)_2$ | H | H | $CH_3$ | $CH_3$ |
| 2-$N(CH_2CH_3)_2$ | 6-$CH_3$ | H | $CH_3$ | $OCH_3$ |
| 4-$SO_2N(CH_2CH_3)_2$ | H | H | $OCH_3$ | $OCH_3$ |
| 4-$N(CH_2CH_3)_2$ | H | H | $CH_3$ | $CH_3$ |

EXAMPLE 12

N-[(4,6-dimethoxypyrimidin-2-yl)aminocarbonyl]-3-pyridinesulfonamide

To 8 ml of 15% aqueous tetrahydrofuran was added with stirring 0.8 g of mercuric acid oxide and 0.56 ml of borontrifluoride etherate. The mixture was stirred for 20 minutes, and then 0.8 g of N-(4,6-dimethoxypyrimidin-2-yl)-N'-(3-pyridinylsulfonyl)carbamimidothioic acid, methyl ester was added. The slurry was stirred at room temperature for 1 hour, filtered, and the solid was rinsed with 50 ml of water, followed by 40 ml of dichloromethane, and dried to give 0.3 g of the desired product, m.p. 176° C. dec.

By using the procedure of Example 12, the compounds of Tables XIII, XIV and XV can be prepared from the appropriately substituted pyridinesulfonylcarbamimidothioic acid esters.

TABLE IX-continued

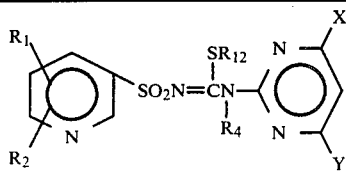

| R₁ | R₂ | R₄ | X | Y | R₁₂ |
|---|---|---|---|---|---|
| 2-CO₂CH—CH=CH(CH₂)₂CH₃ | H | H | CH₃ | OCH₃ | CH₂CH₂CH₃ |
| 2-CO₂CH₂CH₂OCH₃ | H | H | CH₃ | CH₃ | CH₃ |
| 2-CO₂CH₂CH₂OCH₂CH₃ | H | H | CH₃ | OCH₃ | CH₃ |
| 2-CO₂CH₂CH₂CH₂OCH₃ | H | H | CH₃ | OCH₃ | CH₃ |
| 2-CO₂CH₂CH₂Cl | H | H | OCH₃ | OCH₃ | CH₃ |
| 2-CO₂CH₃ | H | H | CH₃ | S(CH₂)₂CO₂C₂H₅ | CH₃ |
| 4-CO₂C₂H₅ | H | H | OCH₃ | OCH₃ | CH₃ |
| 4-OCH₃ | H | H | CH₃ | OCH₃ | CH₃ |
| 4-Cl | H | H | CH₃ | N(CH₃)₂ | CH₃ |
| 4-S—n-C₄H₉ | H | H | OCH₃ | OCH₃ | CH₃ |
| 2-SC₂H₅ | H | H | CH₃ | OCH₃ | CH₃ |
| 4-F | H | H | CH₃ | OCH₂CH₂CO₂C₂H₅ | CH₃ |
| 2-Cl | 4-Cl | H | OCH₃ | OCH₃ | CH₃ |
| 2-Cl | 4-Cl | H | CH₃ | OCH₃ | CH₃ |
| H | H | H | CH₃ | CH₃ | CH₃ |
| H | H | H | OCH₃ | OCH₃ | CH₃ |
| 2-Cl | H | H | OCH₃ | OCH₃ | CH₃ |
| 2-Cl | H | H | CH₃ | —CH₂OCH₃ | CH₃ |
| 2-F | H | H | CH₃ | CH₃ | CH₃ |
| 2-CO₂CH₃ | H | H | OCH₃ | OCH | CH₃ |
| 2-CO₂CH₃ | H | H | CH₃ | OCH₃ | CH₃ |
| 2-CO₂CH₃ | H | H | CH₃ | CH₃ | CH₃ |
| 2-CO₂—i-C₃H₇ | H | H | CH₃ | CH₃ | CH₃ |
| 2-CO₂—i-C₃H₇ | H | H | CH₃ | OCH₃ | CH₃ |
| 2-CO₂—i-C₃H₇ | H | H | OCH₃ | OCH₃ | CH₃ |
| 2-CH₃ | H | H | OCH₃ | OCH₃ | CH₂CH₂CH₂CH₃ |
| 2-CH₃ | H | H | CH₃ | OCH₃ | CH₃ |
| 2-CH₃ | H | H | CH₃ | CH₃ | CH₃ |
| 4-Cl | H | H | CH₃ | CH₃ | CH₃ |
| 4-Br | H | H | OCH₃ | OCH₃ | CH₃ |
| 4-CO₂CH₃ | H | H | CH₃ | CH₃ | CH₃ |
| 4-CO₂CH₃ | H | H | CH₃ | OCH₃ | CH₃ |
| 4-CO₂CH₃ | H | H | OCH₃ | OCH₃ | CH₃ |
| 4-CO₂—i-C₃H₇ | H | H | CH₃ | CH₃ | CH₂CH₃ |
| 4-CO₂—i-C₃H₇ | H | H | OCH₃ | OCH₃ | CH₃ |
| 4-CO₂—i-C₃H₇ | H | H | OCH₃ | OCH₃ | CH₃ |
| 4-CH₃ | H | H | CH₃ | CH₃ | CH₃ |
| 4-CH₃ | H | H | OCH₃ | OCH₃ | CH₃ |
| 4-SO₂N(CH₂CH₃)₂ | 2-CH₃ | H | CH₃ | OCH₃ | CH₃ |
| 2-N(CH₃)₂ | 6-CH₃ | H | CH₃ | CH₃ | CH₂CH₃ |
| 4-N(CH₃)₂ | H | H | OCH₃ | OCH₃ | CH₃ |
| 4-SO₂N(CH₃)₂ | H | H | CH₃ | OCH₃ | CH₂CH₂CH₂CH₃ |

TABLE X

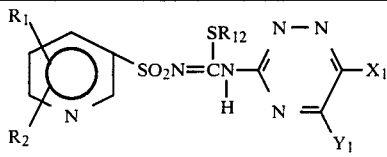

| R₁ | R₂ | Y₁ | X₁ | R₁₂ |
|---|---|---|---|---|
| 2-C₂H₅ | 2-CH₃ | CH₃ | CH₃ | CH₃ |
| 4-CO₂C₂H₅ | H | CH₃ | CH₃ | CH₃ |
| 2-CO₂CH₃ | H | CH₃ | CH₃ | CH₃ |
| 2-SO₂N(CH₂CH₃) | H | CH₃ | CH₃ | CH₃ |
| 4-N(CH₂CH₃) | H | OCH₃ | CH₃ | CH₂CH₃ |
| 2-SO₂N(CH₃)₂ | H | CH₃ | OCH₃ | CH₃ |

TABLE XI

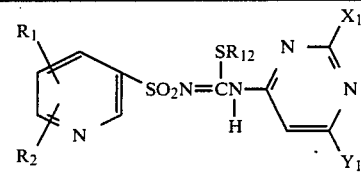

| R₁ | R₂ | Y₁ | X₁ | R₁₂ |
|---|---|---|---|---|
| 2-n-C₄H₉ | H | OCH₃ | CH₃ | CH₃ |
| 4-CO₂CH₃ | H | OCH₃ | Cl | CH₃ |
| 2-Cl | H | OCH₃ | OCH₃ | CH₃ |
| 2-N(CH₃)₂ | 6-CH₃ | CH₃ | CH₃ | CH₃ |
| 4-SO₂N(CH₃)₂ | H | CH₃ | OCH₃ | CH₂CH₂CH₂CH₃ |

EXAMPLE 10

N-[(4-methoxy-6-methyl-1,3-5-triazin-2-yl)aminocarbonyl]3-pyridinesulfonamide

To 4 ml of 15% aqueous tetrahydrofuran was added with stirring 0.4 g of mercuric oxide and 0.28 ml of

TABLE XIII

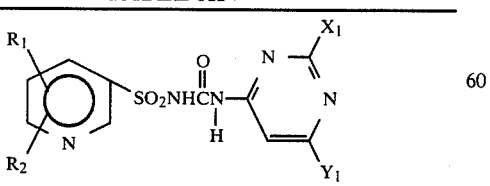

| $R_1$ | $R_2$ | $R_4$ | X | Y |
|---|---|---|---|---|
| 2-Cl | H | $CH_3$ | $CH_3$ | $OCH_3$ |
| 4-Cl | H | H | $CH_3$ | $OCH_3$ |
| 2-$CH_3$ | 6-$CH_3$ | H | $CH_3$ | $OCH_3$ |
| 4-$CH_3$ | H | $CH_3$ | $CH_3$ | $OCH_2CH_2OCH_3$ |
| 2-$CO_2CH_2CH=CH_2$ | H | H | $CH_3$ | $OCH_3$ |
| 2-$CO_2CH-CH=CH(CH_2)_2CH_3$ | H | H | $CH_3$ | $OCH_3$ |
| 2-$CO_2CH_2CH_2OCH_3$ | H | H | $CH_3$ | $CH_3$ |
| 2-$CO_2CH_2CH_2OCH_2CH_3$ | H | H | $CH_3$ | $OCH_3$ |
| 2-$CO_2CH_2CH_2OCH_3$ | H | H | $CH_3$ | $OCH_3$ |
| 2-$CO_2CH_2CH_2Cl$ | H | H | $OCH_3$ | $OCH_3$ |
| 2-$CO_2CH_3$ | H | H | $CH_3$ | $S(CH_2)_2CO_2C_2H_5$ |
| 4-$CO_2C_2H_5$ | H | H | $OCH_3$ | $OCH_3$ |
| 4-$OCH_3$ | H | H | $CH_3$ | $OCH_3$ |
| 2-$OCH_3$ | H | H | $OC_2H_5$ | $OCH_3$ |
| 4-Cl | H | H | $CH_3$ | $N(CH_3)_2$ |
| 4-Br | H | H | $CH_3$ | Cl |
| 4-$OC_2H_5$ | H | H | $CH_3$ | $SC_2H_5$ |
| 4-S—n-$C_4H_9$ | H | H | $OCH_3$ | $OCH_3$ |
| 2-$SC_2H_5$ | H | H | $OCH_3$ | $OCH_3$ |
| 4-F | H | H | $CH_3$ | $OCH_2CH_2CO_2C_2H_5$ |
| 2-$SCH_3$ | H | H | $CH_3$ | $OCH_3$ |
| 2-Br | H | H | $OCH_3$ | $OCH_3$ |
| 2-n-$C_4H_9$ | H | H | $OCH_3$ | $OCH_3$ |
| 4-F | 6-Cl | H | $OC_2H_5$ | $CH_2OCH_3$ |
| 2-$SO_2N(CH_3)_2$ | 6-$CH_3$ | H | $CH_3$ | $OCH_3$ |
| 2-$N(CH_2CH_3)$ | H | H | $OCH_3$ | $OCH_3$ |
| 4-$SO_2N(CH_3)_2$ | 2-$CH_3$ | H | $CH_3$ | $CH_3$ |
| 4-$SO_2N(CH_3)_2$ | H | H | $CH_3$ | $OCH_3$ |
| 2-Cl | 4-Cl | H | $OCH_3$ | $OCH_3$ |
| 2-Cl | 4-Cl | H | $CH_3$ | $OCH_3$ |
| H | H | H | $CH_3$ | $CH_3$ |
| H | H | H | $OCH_3$ | $OCH_3$ |
| 2-Cl | H | H | $OCH_3$ | $OCH_3$ |
| 2-Cl | H | H | $CH_3$ | —$CH_2OCH_3$ |
| 2-Cl | H | H | $CH_3$ | $CH_3$ |
| 2-$CO_2CH_3$ | H | H | $OCH_3$ | OCH |
| 2-$CO_2CH_3$ | H | H | $CH_3$ | $OCH_3$ |
| 2-$CO_2CH_3$ | H | H | $CH_3$ | $CH_3$ |
| 2-$CO_2$—i-$C_3H_7$ | H | H | $CH_3$ | $CH_3$ |
| 2-$CO_2$—i-$C_3H_7$ | H | H | $CH_3$ | $OCH_3$ |
| 2-$CO_2$—i-$C_3H_7$ | H | H | $OCH_3$ | $OCH_3$ |
| 2-$CH_3$ | H | H | $OCH_3$ | $OCH_3$ |
| 2-$CH_3$ | H | H | $CH_3$ | $OCH_3$ |
| 2-$CH_3$ | H | H | $CH_3$ | $CH_3$ |
| 4-Cl | H | H | $CH_3$ | $CH_3$ |
| 4-Cl | H | H | $OCH_3$ | $OCH_3$ |
| 4-$CO_2CH_3$ | H | H | $CH_3$ | $CH_3$ |
| 4-$CO_2CH_3$ | H | H | $CH_3$ | $OCH_3$ |
| 4-$CO_2CH_3$ | H | H | $OCH_3$ | $OCH_3$ |
| 4-$CO_2$—i-$C_3H_7$ | H | H | $CH_3$ | $CH_3$ |
| 4-$CO_2$—i-$C_3H_7$ | H | H | $CH_3$ | $OCH_3$ |
| 4-$CO_2$—i-$C_3H_7$ | H | H | $OCH_3$ | $OCH_3$ |
| 4-$CH_3$ | H | H | $CH_3$ | $CH_3$ |
| 4-$CH_3$ | H | H | $OCH_3$ | $OCH_3$ |

TABLE XIV

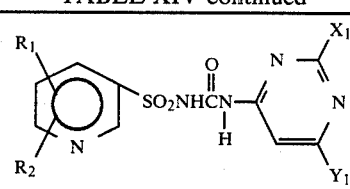

| $R_1$ | $R_2$ | $X_1$ | $Y_1$ |
|---|---|---|---|
| 2-F | H | $CH_3$ | $CH_3$ |
| 2-$C_2H_5$ | H | $CH_3$ | OCH |
| 2-Cl | H | $CH_3$ | $OCH_3$ |
| 4-$C_2H_5$ | 2-$CH_3$ | $CH_3$ | $CH_3$ |
| 4-Br | 6-Cl | $CH_3$ | $OCH_3$ |
| 4-$CO_2C_2H_5$ | H | $CH_3$ | $CH_3$ |

TABLE XIV-continued

[Structure: pyridine ring with R1, R2 substituents, SO2NHC(O)N(H)- linked to triazine ring with X1, Y1]

| R₁ | R₂ | X₁ | Y₁ |
|---|---|---|---|
| 2-CO₂CH₃ | H | CH₃ | CH₃ |
| 4-OCH₃ | H | CH₃ | OCH₃ |
| 2-Br | H | OCH₃ | OCH₃ |
| 2-SO₂N(CH₃)₃ | H | CH₃ | OCH₃ |
| 4-N(CH₂CH₃)₂ | H | OCH₃ | OCH₃ |
| 2-SCH₃ | H | CH₃ | OCH₃ |

TABLE XV

[Structure: pyridine ring with R1, R2, SO2NHC(O)NH- linked to triazole ring with X1, Y1]

| R₁ | R₂ | Y₁ | X₁ |
|---|---|---|---|
| 4-F | H | OCH₃ | C₂H₅ |
| 2-Cl | H | OCH₃ | OCH₃ |
| 2-N(CH₃)₂ | 6-CH₃ | CH₃ | CH₃ |
| 4-SO₂N(CH₃)₂ | H | CH₃ | OCH₃ |

Agriculturally useful acid addition salts of appropriate N-[(triazinyl)aminocarbonyl]pyridinesulfonamides or N-[(pyrimidinyl)aminocarbonyl]pyridinesulfonamides can be prepared as described in Equation 14 by treating the appropriate N-aminocarbonylpyridinesulfonamide with an equivalent amount of a suitable mineral or organic acid in a solvent such as methanol or ethanol and removing the solvent to yield the desired acid salt. By this method, acid addition salts can be prepared with anions such as: Cl⁻, Br⁻, NO₃⁻, HSO₄⁻, SO₄⁼, H₂PO₄⁻, HPO₄⁼, CCl₃COO⁻, CH₃SO₃⁻, p-CH₃C₆H₄SO₃, and C₁₂H₂₅SO₃⁻.

Agriculturally useful alkali metal salts can be prepared as described in Equation 12 by the reaction of a suitable N-[(triazinyl)-aminocarbonyl]pyridinesulfonamide or a N-(pyrimidinylaminocarbonyl)pyridinesulfonamide with an equivalent of a suitable alkali metal alkoxide in an alcohol solvent (for example, sodium methoxide in methanol) removal of solvent and trituration usually performed with a solvent such as ethylacetate. In this manner, a variety of alkali metal salts can be made with cations such as: Li⁺, Na⁺, K⁺, Ca⁺⁺.

It should be noted that there is not intent to be limited to the salts which are mentioned above.

EXAMPLE 13

2-Chloro-N-[(4-methoxy-6-methyl-1,3,5-triazin-2-yl) aminocarbonyl]-3-pyridinesulfonamide, sodium salt.

To a stirred suspension of 1.0 g of 2-chloro-N-[(4-methoxy-6-methyl-1,3,5-triazin-2-yl)aminocarbonyl]3-pyridinesulfonamide in 25 ml of methanol is added 0.15 g of sodium methoxide. The resulting solution is heated on a steam bath for 5 minutes, cooled and the solvent removed in vacuo to yield the desired salt Trituration with ethylacetate yields the sodium salt of 2-chloro-N-[(4-methoxy-6-methyl-1,3,5-triazin-2-yl)aminocarbonyl]-3-pyridinesulfonamide as a colorless solid.

As described in Equation 13 and further illustrated in Example 14, reaction of a suitable N-(triazinylaminocarbonyl)pyridinesulfonamide or a N-(pyrimidinylaminocarbonyl)pyridinesulfonamide with an equivalent of an appropriate amine in a solvent such as methylene chloride or methanol followed by removal of this solvent yields agriculturally useful ammonium salts of N-(aminocarbonyl)pyridinesulfonamides. Amines such as ammonia, ethylamine, diethylamine, triethylamine, trimethylamine, diethanolamine, triethanolamine, isopropylamine, pyridine, dimethylaniline, laurylamine or di-n-butylamine may be employed.

EXAMPLE 14

2-Chloro-N-[(4-methoxy-6-methylpyrimidin-2-yl)aminocarbonyl]-3-pyridinesulfonamide, triethanolamine salt To a stirring suspension of 1.0 g of 2-chloro-N-[(4-methoxy-6-methylpyrimidin-2-yl)aminocarbonyl]-3-pyridinesulfonamide in 25 ml of methylene chloride is added 0.42 g of triethanolamine. The solvent is removed in vacuo to yield as product the desired triethanolamine salt.

By using an appropriately substituted N-alkylpyridinesulfonylcarbamyl chloride or thiocarbamyl-chloride and an appropriate aminopyrimidine or aminotriazine, the compounds of Formula I set forth in Table XVI can be prepared by the procedure of Equation 5. For example, 2-chloro-N-[N-(4-methoxy6-methyl-pyrimidine-2-yl)-N-methylaminocarbonyl]-N-methyl-3-pyridinesulfonamide can be prepared by reacting 2.1 g of N-[(2-chloro-3-pyridine)sulfonyl]-N'-methylcarbamylchloride in 50 ml of tetrahydrofuran containing 1.0 g of triethylamine to 1.5 g of 2-methylamino-4-methoxy-6-methylpyrimidine. That mixture can be stirred at reflux for several hours, the precipitated salts can be filtered off and the filtrate can be concentrated to yield the desired product.

TABLE XVI

[Structure: pyridine ring with R1, R2, SO2N(CH3)-C(W)-N(R4)- linked to heterocycle with X, Y, Z]

| R₁ | R₂ | R₄ | W | X | Y | Z |
|---|---|---|---|---|---|---|
| 2-Cl | H | H | O | OCH₃ | OCH₃ | CH |
| 2-Cl | H | H | O | CH₃ | OCH₃ | N |
| 2-Cl | H | CH₃ | S | CH₃ | OCH₃ | CH |
| 2-Cl | H | H | O | CH₃ | OCH₃ | CH |
| 2-CO₂CH₃ | H | H | O | CH₃ | N(CH₃)₂ | CH |
| 2-CO₂CH₃ | H | H | O | CH₃ | N(CH₃)₂ | N |
| 4-OC₂H₅ | 6-CH₃ | H | O | CH₃ | OCH₃ | CH |
| 2-SO₂N(CH₃)CH₂CH₃ | H | H | S | CH₃ | OCH₃ | CH |
| 4-N(CH₂CH₃)₂ | H | CH₃ | O | OCH₃ | OCH₃ | N |
| 2-SCH₃ | H | H | O | CH₃ | CH₃ | N |
| 4-Br | H | H | O | CH₃ | N(CH₃)₂ | CH |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE XVII

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley & Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 15

| Wettable Powder | |
|---|---|
| 2-Chloro-N—[(4-methoxy-6-methylpyrimidin-2-yl)aminocarbonyl]-3-pyridinesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 16

| Wettable Powder | |
|---|---|
| 2-Chloro-N—[(4,6-dimethoxypyrimidin-2-yl)aminocarbonyl]-3-pyridinesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 17

| Granule | |
|---|---|
| Wettable Powder of Example 16 | 5% |
| attapulgite granules (U.S.S. 20–40 mesh; 0.84–0.42 mm) | 95% |

A slurry of wettable powder containing 25% solids is sprayed on the surface of attapulgite granules in a double-cone blender. The granules are dried and packaged.

EXAMPLE 18

| Extruded Pellet | |
| --- | --- |
| 2-Chloro-N—[(4,6-dimethylpyrimidin-2-yl)amino-carbonyl-3-pyridinesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 19

| Oil Suspension | |
| --- | --- |
| 2-Chloro-N—[(4-methoxy-6-methyl-1,3,5-triazin-2-yl)aminocarbonyl]-3-pyridinesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 20

| Wettable Powder | |
| --- | --- |
| 2-Chloro-N—[(4,6-dimethoxy-1,3,5-triazin-2-yl)aminocarbonyl]-3-pyridinesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 21

| Low Strength Granule | |
| --- | --- |
| 2-Chloro-N—[(4,6-dimethyl-1,3,5-triazin-2-yl)-aminocarbonyl]-3-pyridinesulfonamide | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 22

| Aqueous Suspension | |
| --- | --- |
| 2-Chloro-N—[(4-methoxy-6-methyl-1,3,5-triazin-2-yl)aminocarbonyl]-3-pyridinesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 23

| Solution | |
| --- | --- |
| 2-Chloro-N—[(4-methoxy-6-methylpyrimidin-2-yl)-aminocarbonyl]-3-pyridinesulfonamide sodium salt | 5% |
| water | 95% |

The salt is added directly to the water with stirring to produce the solution, which may then be packaged for use.

EXAMPLE 24

| Low Strength Granule | |
| --- | --- |
| 2-Chloro-N—[(4,6-dimethyl-1,3,5,triazin-2-yl)-aminocarbonyl]-3-pyridinesulfonamide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 25

| Granule | |
| --- | --- |
| 2-Chloro-N—[(N—4,6-dimethoxy-1,3,5-triazin-2-yl)aminocarbonyl]-3-pyridinesulfonamide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 26

| High Strength Concentrate | |
|---|---|
| 2-Chloro-N—[(4,6-dimethoxypyrimidin-2-yl)-aminocarbonyl]-3-pyridinesulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 27

| Wettable Powder | |
|---|---|
| 2-Chloro-N—[(4,6-dimethylpyrimidin-2-yl)-aminocarbonyl]-3-pyridinesulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 28

| Wettable powder | |
|---|---|
| 2-Chloro-N—[(4-methoxy-6-methyl-1,3,5-triazin-2-yl)aminocarbonyl]-3-pyridinesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 29

| Oil Suspension | |
|---|---|
| 2-Chloro-N—[(4,6-dimethyl-1,3,5-triazin-yl)-aminocarbonyl]-3-pyridinesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 30

| Dust | |
|---|---|
| 2-Chloro-N—[(4,6-dimethoxy-1,3,5-triazin-2-yl)-aminocarbonyl]-3-pyridinesulfonamide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

UTILITY

The compounds of the present invention are active herbicides. They have utility for broad-spectrum pre- and/or post-emergence weed control in areas where complete control of all vegetation is desired, such as around fuel storage tanks, ammunition depots, industrial storage areas, oil-well sites, drive-in theaters, around billboards, highway and railroad structures. By properly selecting rate, time and method of application, compounds of this invention may also be used to modify plant growth beneficially, or to selectively control weeds in crops such as rice and wheat.

The precise amount of the compounds of Formula I to be used in any given situation will vary according to the particular end result desired, the amount of foliage present, the crop species involved, the types of weeds to be controlled, the soil type, the formulation and mode of application, weather conditions, etc. Since so many variables play a role, it is not possible to state a rate of application suitable for all situations. Broadly speaking, the compounds of this invention are used at levels of about (0.01 to 20 kg/ha) with a preferred range of (0.03 to 10 kg/ha). In general, the lower rates of application from within this range are suggested for use on lighter soils and/or those having a low organic matter content, for selective weed control or for plant growth regulation, whereas the higher rates will be selected for adverse conditions or where extended persistence in soil is desired.

The compounds of the invention may be used in combination with any other commercial herbicide examples of which are those of the triazine, triazole, uracil, urea, amide, diphenylether, carbamate bipyridylium types.

The compounds of Formula I may be combined with other herbicides and are particularly useful in combination with 3-(3,4-dichlorophenyl)-1,1-dimethyl urea; the triazines such as 2-chloro-4-(ethylamino)-6-(isopropylamino)-s-triazine: the uracils such as 5-bromo-3-secbutyl-6-methyluracil; N-(phosphonomethyl)glycine; 3-cyclohexyl-1-methyl-6-dimethylamino-s-triazine-2,4-(1H,3H)-dione; N,N-dimethyl-2,2-diphenylacetamide; 2,4-dichlorophenoxyacetic acid (and closely related compounds); 4-chloro-2-butynyl-3-chlorophenylcarbamate; diisopropylthiolcarbamic acid, ester with 2,3-dichloroallyl alcohol; diisopropylthiolcarbamic acid, S-(2,3,3-trichloroallyl)ester; ethyl-N-(benzoyl-N-(3,4-dichlorophenyl)-2-aminopropionate; 1,2-dimethyl-3,5-diphenylpyrazolium methylsulfate; methyl 2-[4-(2,4-dichlorophenoxy)-phenoxy]propanoate; 4-amino-6-tert-butyl-3-(methylthio)-1,2,4-triazin-5(4H)-one; 3-(3,4-dichlorophenyl)-1-methoxy-1-methylurea; 3-isopropyl-1H-2,1,3-benzothiodiazin-(4)-3H-one-2,2-dioxide; $\alpha,\alpha,\alpha$-trifluoro-2,6-dinitro-N,N-dipropyl-p-toluidine; 1,1'-dimethyl-4,4'-bipyridinium ion; monosodium methanearsonate; 2-chloro-2',6'-diethyl(methoxymethyl)acetanilide; and 1,1-dimethyl-3-($\alpha,\alpha,\alpha$-trifluoro-m-tolyl)urea.

The activity of these compounds was discovered in greenhouse tests. The tests are described and the data resulting from them are shown below.

O = no effect
10 = maximum effect
C = chlorosis or necrosis
D = defoliation
E = emergence inhibition
G = growth retardation
H = formative effects
U = unusual pigmentation
S = albinism
X = axillary stimulation
6Y = abscised buds or flowers
6F = delayed flowering.

Test A

Seeds of crabgrass (Digitaria spp.), barnyardgrass (*Echinochloa crusgalli*), wild oats (*Avena fatua*), cassia (*Cassia tora*), morningglory (Ipomoea sp.), cocklebur (Xanthium spp.), sorghum, corn, soybean, rice, wheat and nutsedge tubers (*Cyperus rotundus*) were planted in a growth medium and treated pre-emergence with the chemicals dissolved in a non phytotoxic solvent solution of the compounds of Table XVIII. At the same time, cotton having five leaves (including cotyledonary ones), bush beans with the third trifoliate leaf expanding, crabgrass, barnyardgrass and wild oats with two leaves, cassia with three leaves (including cotyledonary ones), morningglory and cocklebur with four leaves (including the cotyledonary ones), sorghum and corn with four leaves, soybean with two cotyledonary leaves, rice with three leaves, wheat with one leaf, and nutsedge with three to five leaves were sprayed with a non-phytotoxic solvent solution of the compounds of Table XVIII. Other containers of the above untreated weeds and crops were treated pre- or post-emergence with the same non-phytotoxic solvent so as to provide a solvent control. A set of untreated control plants was also included for comparison. Pre-emergence and post-emergence treated plants and controls were maintained in a greenhouse for sixteen days, then all treated plants were compared with their respective controls and rated visually for response to treatment. The data in Table XVIII shows that the compounds of this invention are very effective as herbicides and often cause little or no injury to crops such as wheat and rice.

TABLE XVIII
POSTEMERGENCE
| | Rate kg/ha | BUSH BEAN | COTTON | MORNING-GLORY | COCKLE-BUR | CASSIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| 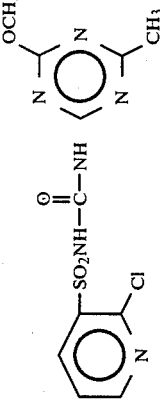 | 0.4 | 9C | 9C | 10C | 10C | 9C | 10C | 9C | 10C | 2C,5G | 5C,7G | 10C | 9C | 9C | 9C |
| 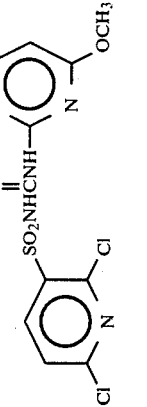 | 0.4 | 9C | 9C | 10C | 10C | 9C | 10C | 9C | 10C | 5C,9G | 5C,8G | 10C | 9C | 9C | 10C |
| 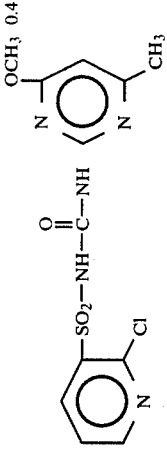 | 0.4 | 9D 2C 9G | 5C 8G | 3C 7G | 3C | 3C | 1C | 2G | 2C 5H | 0 | 0 | 7H | | | |
| 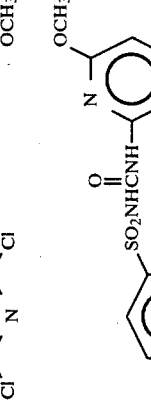 | 0.4 | 5C 8G 6Y | 4C 8G | 1C 6G | 3C 8G | 3C 8G | 9G | 1C 4G | 2C 8H | 1C | 1C | 2U 8H | 2C 5G | 1C 6G | 3C |
| 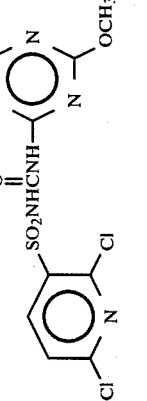 | 0.4 | 4C 8G 6Y | 4C 8G | 1C | 1C | 3C | 0 | 0 | 2C | 0 | 0 | 1C 3H | 3C 7G | 3C 7G | 2C 7G |
| | | | | | | | | | | | | | 1C 3H | 2C 5G | 1C 6G | 1C 3G |

TABLE XVIII-continued

| Structure | | | | | | | | | | | | | | | |
|---|---|---|---|---|---|---|---|---|---|---|---|---|---|---|---|
| ![structure 1: 4-CH3, 6-OCH3 pyrimidine, 2,6-dichloropyridine sulfonylurea] | 0.4 | 9D 9G 6Y | 5C 9G | 10C | 9C | 3C 7G | 2C 8G | 1C | 2C 8H | 1C 2G 3G | 2U 8G | 5C 8G | 5C 7G | 5C 8G |
| ![structure 2: 4,6-diOCH3 pyrimidine N-methyl, 2-chloropyridine sulfonylurea] | 0.4 | 3S 7G 6Y | 5C 8G | 9C | | 2C 8G | 7G | 2G | 2C 9H | 0 | 5C 9G | 2C 7G | 2C 6G | 3G |
| ![structure 3: 4,6-diOCH3 pyrimidine, 2-chloropyridine sulfonylurea] | 0.4 | 9C | | 9C | | 10C | | 9C | 9C | 0 | 5C 9G | 5C 9G | 5C 9G | 9C |
| ![structure 4: 4,6-diOCH3 pyrimidine, 2-chloropyridine sulfonylurea] | 0.4 | 6C 9G 6Y | 6C 8G | 10C | 10C | 5C 9G | 9C | 6G | 5C 9H | 3C 7G 3C 7G | 6U 9G | 5C 9G | 5C 9G | 2C 8G |
| ![structure 5: 4,6-diCH3 pyrimidine, 2-chloropyridine sulfonylurea] | 0.4 | 4C 9G 6Y | 3C 6G | 3C 8G | 2C 8H | 2C 5G | 2C 8G | 9C | 2C | 2C | 9U 9C | 5C 9G | 6C 9G | 2C 8G |
| | | | | | | | | | 4C 9H | 2C | 9C | 4C | 4C | 4C |

TABLE XVIII-continued

| Structure | | | | | | | | | | | | | |
|---|---|---|---|---|---|---|---|---|---|---|---|---|---|
| Pyridine-SO₂NHCNH-pyrimidine(2,6-diCH₃) | 0.4 | 3S 5G 6Y | 2C | 2C 5G | 1C | 1C | 3G | 0 | 0 | 0 | 0 | 0 | 0 |
| Pyridine-SO₂NHCNH-pyrimidine(2,6-diCH₃) | 2 | 1C 3G | 3C 4G | 1C | 3C 9G | 2C | 0 | 0 | 0 | 0 | 1G | 1C | 7G 3G |
| Pyridine-SO₂NHCNH-pyrimidine(2,6-diOCH₃) | 2 | 5C 8G 6Y | 5C 9G | 9C | 10C | 3C 8G | 5C 9G | 1C 3G | 4G | 0 | 1C 3G | 2C 9G | 2C 9G 4G |
| Pyridine-SO₂NHCNH-pyrimidine(2-CH₃,6-OCH₃) | 2 | 4C 7G 6Y | 2C 4H | 0 | 3C 9G | 1C | 1C 5G | 0 | 0 | 0 | 2G | 3C 7G | — 2G |
| 6-Cl-Pyridine-SO₂NHCNH-pyrimidine(2-CH₃,6-OCH₃) | 2 | 4C 6G 6Y | 5C 9G | 5C 9G · 3C 9G | 0 | 0 | 0 | 0 | 0 | 2C 3H | 0 | 0 |

TABLE XVIII-continued

| Structure | Rate kg/ha | MORN-ING GLORY | COCKLE-BUR | CASSIA | NUT-SEDGE | CRAB-GRASS | BARNYARD GRASS | WILD OATS | WHEAT | CORN | SOYBEAN | RICE | SORGHUM |
|---|---|---|---|---|---|---|---|---|---|---|---|---|---|
| Pyridine-SO₂NHCNH-pyrimidine(OCH₃)₂, Cl | 2 | 3C 7G 6Y | 4C 9G | 3C 7H | 2C 8G | 2C | 7G | 0 | 0 | 0 | 0 | 0 | 3C 7G 7G 0 |
| Pyridine-SO₂NHCNH-pyrimidine(OCH₃)₂, Cl | 2 | 2G | 0 | 0 | 0 | 0 | 0 | 0 | 0 | 0 | 0 | 0 | 0 |
| Pyridine-SO₂NHCNH-pyrimidine(OCH₃)₂, Cl | 2 | 2C | 2C 2H | 0 | 0 | 0 | 0 | 0 | 0 | 0 | 0 | 0 | 0 |
| Pyridine-SO₂NHCNH-pyrimidine(CH₃,OCH₃), Cl | 2 | 2C 3H | 2C 3H | 2C 6H | 7H | 1C | 0 | 0 | 0 | 0 | 0 | 0 | 0 |

PREEMERGENCE

| Structure | Rate kg/ha | MORN-ING GLORY | COCKLE-BUR | CASSIA | NUT-SEDGE | CRAB-GRASS | BARNYARD GRASS | WILD OATS | WHEAT | CORN | SOYBEAN | RICE | SORGHUM |
|---|---|---|---|---|---|---|---|---|---|---|---|---|---|
| 2-Cl-pyridine-SO₂NH-C(O)-NH-pyrimidine(OCH₃,CH₃) | 0.4 | 9C | 9H | 3C,9G | 8G | 4C,9G | 10C | 9H | 9H | 10E | 9H | 10E | 10H |

TABLE XVIII-continued

| Structure | | | | | | | | | | | | | | | |
|---|---|---|---|---|---|---|---|---|---|---|---|---|---|---|---|
| ![structure with 2-Cl pyridine, SO2NH-C(=O)-NH, OCH3/CH3 pyrimidine] | 0.4 | 9G | 9H | 5C,9G | 10E | 5C,9G | 10H | 5C,9G | 10E | 10E | 9H | 10E | 10H | | |
| ![structure with 2,6-diCl pyridine, SO2NHCNH, CH3/OCH3 pyrimidine] | 0.4 | 2G | 1C | 3C | 1C 4G | 2G | 1C 6G | 0 | 0 | 2C 3G | 2C 3G | 3C | 3C 6G | | |
| ![structure with 2,6-diCl pyridine, SO2NHCNH, OCH3/OCH3 pyrimidine] | 0.4 | 8G | 8G | 8G | 10E | 1C 5G | 3C 9H | 1C 5G | 7G | 9G | 9H | 10E | 1C 9G | | |
| ![structure with 2,6-diCl pyridine, SO2NHCNH, OCH3/CH3 pyrimidine] | 0.4 | 2C | 0 | 2C | 1C 5G | 2G | 1C | 0 | 0 | 1C 2G | 1C | 1C 5G | 1C 2G | | |
| ![structure with 2,6-diCl pyridine, SO2NHCNH, CH3/OCH3 pyrimidine] | 0.4 | 9G | 8G | 8G | 10E | 2G | 2C 8H | 1C 5G | 1C 5G | 1C 9G | 2C 5H | 9H | 1C 9G | | |

TABLE XVIII-continued

| Structure | | | | | | | | | | | | | |
|---|---|---|---|---|---|---|---|---|---|---|---|---|---|
| 2-Cl-pyridyl-SO₂NHC(=O)N(CH₃)- [4,6-di-OCH₃-pyrimidinyl] | 0.4 | 9G | 3G | 1C 4G | 0 | 0 | 4H | 0 | 0 | 1C 3G 2C | 1C 3H 2G |
| 2-Cl-pyridyl-SO₂NHC(=O)NH- [4,6-di-OCH₃-pyrimidinyl, 5-position attach] | 0.4 | 9G | 9G | 9G | 10E | 9H | 5C 9H | 2C 7G 9H | 10E 9H | 10E 9H |
| 2-Cl-pyridyl-SO₂NHC(=O)NH- [4,6-di-OCH₃-pyrimidinyl] | 0.4 | 9C | 9G | 9G | 4G | 9H | 9H | 4G | 2C 9H | 10E 9H | 10E 5C 9H |
| 2-Cl-pyridyl-SO₂NHC(=O)NH- [4,6-di-CH₃-pyrimidinyl] | 0.4 | 6G | 0 | 2C 5G | 0 | 0 | 2C 9H | 0 | 8H | 3C 9G 1C | 9H 2C 9G |
| pyridyl-SO₂NHC(=O)NH- [4,6-di-CH₃-pyrimidinyl] | 0.4 | 3G | 0 | 0 | 0 | 0 | 0 | 0 | 0 | 0 | 0 |

TABLE XVIII-continued

| Structure | | | | | | | | | | | |
|---|---|---|---|---|---|---|---|---|---|---|---|
| 3,5-dimethyl-pyridin-2-yl sulfonylurea (CH$_3$, CH$_3$ pyrimidine) | 2 | 6G | 8G | 1C 8G | 0 | 0 | 4G | 0 | 2H | 2G | 0 |
| 3,5-dimethoxy-pyridin-2-yl sulfonylurea (OCH$_3$, OCH$_3$ pyrimidine) | 2 | 9G | 10E | 1C 9G | 10E | 5G | 3C 8H | 8G | 9G | 9H | 10E 2C 9H |
| 3-methyl-5-methoxy-pyridin-2-yl sulfonylurea (CH$_3$, OCH$_3$ pyrimidine) | 2 | 8G | 1C | 2C 7G | 0 | 1C | 0 | 0 | 2C 7G | 2C | 1C |
| 6-chloropyridin-3-yl sulfonylurea (CH$_3$, OCH$_3$ pyrimidine) | 2 | 7G | 7G | 2C | 4G | 2G | 2G | 0 | 0 | 5G 3C | 8G 0 |
| 6-chloropyridin-3-yl sulfonylurea (OCH$_3$, OCH$_3$ pyrimidine) | 2 | 9G | 9H | 2C 5G | 10E | 0 | 2C 4H | 1C | 1C | 1C 8G 1C 2G | 9H 2G |

TABLE XVIII-continued

| Structure | R | | | | | | | | | | | | | |
|---|---|---|---|---|---|---|---|---|---|---|---|---|---|---|
| 6-chloro-pyridin-3-yl-SO₂NHC(O)NH– / 4,6-di-OCH₃ pyrimidine | 2 | 0 | 0 | 0 | 0 | 0 | 0 | 0 | 0 | 0 | 0 | 0 | 0 | 0 |
| 6-chloro-pyridin-3-yl-SO₂NHC(O)NH– / 4,6-di-OCH₃ pyrimidine | 2 | 6H | 2C | 0 | 0 | 0 | 0 | 0 | 0 | 0 | 0 | 0 | 0 | 0 |
| 6-chloro-pyridin-3-yl-SO₂NHC(O)NH– / 4-CH₃-6-OCH₃ pyrimidine | 2 | 0 | 0 | 0 | 0 | 0 | 0 | 2C 2G | 1C | 5G | 0 | 0 | 0 | 0 |

Test B

Two plastic bulb pans were filled with fertilized and limed Fallsington silt loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pennsylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugarbeets. The above four containers were treated pre-emergence with several test compounds within the scope of the invention.

Twenty-eight days after treatment, the plants were evaluated and visually rated for response to the chemical treatments utilizing the rating system described previously for Test A. The data are summarized in Table XIX. Note that the compounds are useful as pre-emergence treatments for weed control in crops such as soybeans.

TABLE XIX
SECONDARY PRE-EMERGENCE ON FALLSINGTON SILT LOAM

Compound

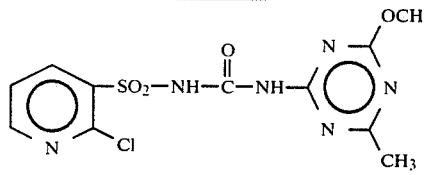

| | Rate, kg/ha | |
|---|---|---|
| | 0.06 | 0.25 |
| Crabgrass | 7G | 10C |
| Barnyardgrass | 9G,9C | 10C |
| Sorghum | 10C | 10E |
| Wild Oats | 0 | 4G |
| Johnsongrass | 9G,9C | 10C |
| Dallisgrass | 5G | 7G |
| Giant Foxtail | 10C | 10C |
| Ky. Bluegrass | 10E | 10E |
| Cheatgrass | 8G,9C | 10C |
| Sugarbeets | 10C | 10C |
| Corn | 10C | 10E |
| Mustard | 10C | 10C |
| Cocklebur | 8G,5H | 8G,9H |
| Pigweed | 10E | 10E |
| Nutsedge | 5G | 7G |
| Cotton | 8G | 8G |
| Morningglory | 8G,7C | 10C |
| Cassia | 8G,8C | 8G,9C |
| Teaweed | 10C | 10C |
| Velvetleaf | 8G,8C | 10C |
| Jimsonweed | 7G | 8G,9C |
| Soybean | 10E | 10E |
| Rice | 4G | 7G,3C |
| Wheat | | |

Compound

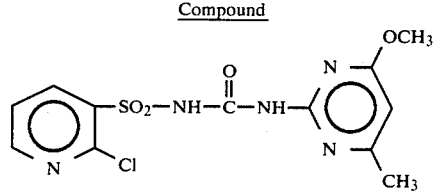

| | 0.06 | 0.25 |
|---|---|---|
| Crabgrass | 9G,6C | 10C |
| Barnyardgrass | 10C | 10C |
| Sorghum | 10C | 10E |
| Wild Oats | 7G,3C | 10C |
| Johnsongrass | 9G,9C | 10C |
| Dallisgrass | 9G,5C | 10C |
| Giant Foxtail | 10C | 10C |
| Ky. Bluegrass | 10E | 10E |
| Cheatgrass | 10E | 10E |
| Sugarbeets | 10C | 10C |
| Corn | 9G,8C | 10E |
| Mustard | 10C | 10C |
| Cocklebur | 8G,5H | 8G,8H |
| Pigweed | 10E | 10E |
| Nutsedge | 8G | 10E |
| Cotton | 8G | 8G |
| Morningglory | 8G,8C | 8G,8C |
| Cassia | 8G,8C | 8G,8C |
| Teaweed | 10C | 10C |
| Velvetleaf | 10C | 10C |
| Jimsonweed | 8G,8C | 8G,9C |
| Soybean | 8G,8C | 8G,9C |
| Rice | 10E | 10E |
| Wheat | 10C | 10C |

Test C

Two compounds, 2-chloro-N-[(4-methoxy-6-methyl-1,3,5-triazin-2-yl)aminocarbonyl-3-pyridinesulfonamide, (Compound A) and 2-chloro-N-[(4-methoxy-6-methylpyrimidin-2-yl)aminocarbonyl], (Compound B), were applied pre- and post-emergence to a number of crops and weeds under field conditions. The post-emergence treatment was applied 20 days after planting the crops. The following data show that one or the other of the two compounds exhibits pre- and/or post-emergence selectivity on cucumber, squash, flax, wheat, oats and tomato.

TABLE XX

| Materials | Rate, Active kg/ha | % Control Overall Grasses 5 Weeks | Grasses 11 Weeks | Broadleaves 5 Weeks | Broadleaves 11 Weeks | % Control - 5 weeks Flax | Tomato | Cucumber | Squash | Oats | Wheat |
|---|---|---|---|---|---|---|---|---|---|---|---|
| | | | | Pre-Emergence | | | | | | | |
| Comp. A | .015 | 50 | 0 | 65 | 50 | 0 | 20 | 0 | 20 | 0 | 0 |
| | .031 | 70 | 20 | 92 | 80 | 0 | 30 | 30 | 30 | 0 | 0 |
| | .063 | 85 | 30 | 98 | 80 | 20 | 20 | 25 | 70 | 15 | 10 |
| Comp. B | .015 | 98 | 80 | 100 | 99 | 0 | 30 | 0 | 20 | 70 | 30 |

TABLE XX-continued

| Materials | Rate, Active kg/ha | % Control Overall | | | | % Control - 5 weeks | | | | | |
|---|---|---|---|---|---|---|---|---|---|---|---|
| | | Grasses | | Broadleaves | | | | | | | |
| | | 5 Weeks | 11 Weeks | 5 Weeks | 11 Weeks | Flax | Tomato | Cucumber | Squash | Oats | Wheat |
| | .031 | 100 | 80 | 100 | 98 | 15 | 50 | 25 | 20 | 72 | 55 |
| | | | | Post-Emergence | | | | | | | |
| Comp. A | .015 | 80 | 50 | 90 | 50 | 0 | 80 | 0 | 70 | 0 | 0 |
| | .031 | 85 | 90 | 94 | 70 | 0 | 80 | 30 | 95 | 0 | 0 |
| | .063 | 98 | 98 | 98 | 95 | 0 | 98 | 70 | 95 | 0 | 0 |
| Comp. B | .015 | 92 | 95 | 98 | 40 | 30 | 0 | 0 | 55 | 60 | 20 |
| | .031 | 98 | 98 | 98 | 75 | 40 | 0 | 0 | 40 | 70 | 50 |
| | .063 | 99 | 99 | 99 | 90 | 60 | 0 | 30 | 60 | 90 | 70 |

What is claimed is:

1. A compound of the formula:

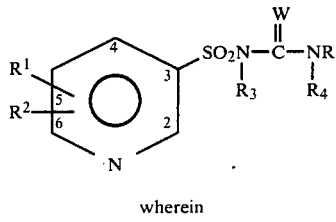

wherein

R is 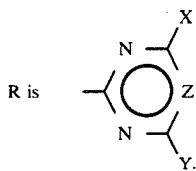

$R_1$ is H, Cl, Br, F, $C_1$-$C_4$ alkyl, $C_1$-$C_4$ alkoxy, $C_1$-$C_4$ alkylthio, $COOR_5$, $NR_6R_7$ or $SO_2NR_{10}R_{11}$;
$R_2$ is H, Cl, Br or $CH_3$;
$R_3$ and $R_4$ are independently H or $CH_3$;
$R_5$ is $C_1$-$C_6$ alkyl, $C_3$-$C_6$ alkenyl, $CH_2CH_2OCH_3$, $CH_2CH_2OCH_2CH_3$, $CH_2CH_2CH_2OCH_3$ or $CH_2CH_2Cl$;
$R_6$ and $R_7$ are independently $CH_3$ or $CH_3CH_2$;
$R_6$ and $R_7$ can be taken together to form —$(CH_2)_4$—, —$(CH_2)_5$— or —$CH_2CH_2OCH_2CH_2$—;
$R_{10}$ and $R_{11}$ are independently $CH_3$ or $CH_3CH_2$;
W is oxygen or sulfur;
X is $CH_3$, —$OCH_3$ or —$OCH_2CH_3$;
Y is H, Cl, $CH_3$, $CF_3$, —$NHCH_3$, —$N(CH_3)_2$—, —$CH_2OR_8$, —$CH_2CH_2OR_8$, —$OCH_2CF_3$ or $VR_9$;
Z is CH;
V is oxygen or sulfur;
$R_8$ is $CH_3$ or $CH_3CH_2$; or
$R_9$ is $CH_3$, $CH_3CH_2$, $CH_2CO_2R_8$, $CH_2CH_2OR_8$, $C(CH_3)HCO_2R_8$ or $CH_2CH_2CO_2R_8$;
and agricultural salts thereof; providing that:
$R_1$ is at the 2- or 4-position of the pyridine ring.

2. A compound of claim 1 wherein $R_3$ is H and W is oxygen.

3. A compound of claim 2 wherein $R_2$ is hydrogen.

4. A compound of claim 3 wherein $R_1$ is Cl, $CH_3O$ or $CH_3$.

5. Compounds of claim 4 wherein $R_1$ is 2- or 4-chloro.

6. A compound of claim 5 wherein $R_4$ is hydrogen.

7. A compound of claim 5 wherein $R_1$ is chlorine.

8. A compound of claim 5 wherein X is $CH_3$ or —$OCH_3$; and Y is $CH_3$, —$OCH_3$, $OCH_2CH_3$ or —$CH_2OCH_3$.

9. A compound of claim 8 wherein $R_3$ and $R_4$ are hydrogen and W is oxygen.

10. The compound of claim 1, 2-chloro-N-[(4-methoxy-6-methylpyrimidin-2-yl)aminocarbonyl)]-3-pyridinesulfonamide.

11. The compound of claim 1, 2-chloro-N-[(4,6-dimethoxypyrimidin-2-yl)aminocarbonyl]-3-pyridinesulfonamide.

12. The compound of claim 1, 2-chloro-N-[(4,6-dimethylpyrimidin-2-yl)aminocarbonyl]-3-pyridinesulfonamide.

13. A composition suitable for controlling the growth of undesired vegetation which comprises an effective amount of a compound of claim 1 and at least one of the following: surfactant, solid or liquid diluent.

14. A composition suitable for controlling the growth of undesired vegetation which comprises an effective amount of a compound of claim 2 and at least one of the following: surfactant, solid or liquid diluent.

15. A composition suitable for controlling the growth of undesired vegetation which comprises an effective amount of a compound of claim 3 and at least one of the following: surfactant, solid or liquid diluent.

16. A composition suitable for controlling the growth of undesired vegetation which comprises an effective amount of a compound of claim 4 and at least one of the following: surfactant, solid or liquid diluent.

17. A composition suitable for controlling the growth of undesired vegetation which comprises an effective amount of a compound of claim 5 and at least one of the following: surfactant, solid or liquid diluent.

18. A composition suitable for controlling the growth of undesired vegetation which comprises an effective amount of a compound of claim 6 and at least one of the following: surfactant, solid or liquid diluent.

19. A composition suitable for controlling the growth of undesired vegetation which comprises an effective amount of the compound of claim 7 and at least one of the following: surfactant, solid or liquid diluent.

20. A method for controlling the growth of undesired vegetation which comprises applying to the locus to be protected an effective amount of a compound of claim 1.

21. A method for controlling the growth of undesired vegetation which comprises applying to the locus to be protected an effective amount of a compound of claim 2.

22. A method for controlling the growth of undesired vegetation which comprises applying to the locus to be protected an effective amount of a compound of claim 3.

23. A method for controlling the growth of undesired vegetation which comprises applying to the locus to be protected an effective amount of a compound of claim 4.

24. A method for controlling the growth of undesired vegetation which comprises applying to the locus to be protected an effective amount of a compound of claim 5.

25. A method for controlling the growth of undesired vegetation which comprises applying to the locus to be protected an effective amount of a compound of claim 6.

26. A method for controlling the growth of undesired vegetation which comprises applying to the locus to be protected an effective amount of the compound of claim 7.

* * * * *